United States Patent
Wu et al.

(10) Patent No.: US 11,317,816 B1
(45) Date of Patent: May 3, 2022

(54) MULTI-WAVELENGTH PULSE OXIMETRY

(71) Applicant: Fitbit, Inc., San Francisco, CA (US)

(72) Inventors: Anjian Wu, Colma, CA (US); Chris H. Sarantos, San Francisco, CA (US); Peter W. Richards, San Francisco, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 98 days.

(21) Appl. No.: 16/798,257

(22) Filed: Feb. 21, 2020

Related U.S. Application Data

(63) Continuation of application No. 15/376,542, filed on Dec. 12, 2016, now Pat. No. 10,568,525.
(Continued)

(51) Int. Cl.
*A61B 5/0205* (2006.01)
*A61B 5/1455* (2006.01)
(Continued)

(52) U.S. Cl.
CPC .......... *A61B 5/0205* (2013.01); *A61B 5/0004* (2013.01); *A61B 5/0022* (2013.01);
(Continued)

(58) Field of Classification Search
CPC ..... A61B 5/0205; A61B 5/6824; A61B 5/742; A61B 5/0004; A61B 5/7278;
(Continued)

(56) References Cited

U.S. PATENT DOCUMENTS 3,608,545 A 9/1971 Novack et al.
4,258,719 A 3/1981 Lewyn
(Continued)

FOREIGN PATENT DOCUMENTS

CN 1623175 A 6/2005
CN 1729933 8/2006
(Continued)

OTHER PUBLICATIONS

U.S. Office Action, dated Aug. 4, 2014, issued in U.S. Appl. No. 13/924,784.
(Continued)

*Primary Examiner* — Eric F Winakur
*Assistant Examiner* — Abid A Mustansir
(74) *Attorney, Agent, or Firm* — Dority & Manning, P.A.

(57) ABSTRACT

In one embodiment, a method for creating a blood oxygen saturation ($SpO_2$) value, the method comprises receiving one or more photoplethysmography (PPG) signals for $SpO_2$ detection from one or more PPG sensors; receiving one or more PPG signals for characterizing a heart rate from the one or more PPG sensors; using the one or more PPG signals for $SpO_2$ detection, forming one or more $SpO_2$ datasets wherein the $SpO_2$ datasets respectively comprise one or more noise components; removing the one or more noise components from the one or more $SpO_2$ datasets that are inconsistent with a feature of the one or more PPG signals characterizing the heart rate to produce one or more filtered $SpO_2$ datasets; and using the one or more filtered $SpO_2$ datasets, creating and storing the $SpO_2$.

17 Claims, 9 Drawing Sheets

Related U.S. Application Data

(60) Provisional application No. 62/266,793, filed on Dec. 14, 2015.

(51) Int. Cl.
*A61B 5/00* (2006.01)
*A61B 5/024* (2006.01)

(52) U.S. Cl.
CPC ........ *A61B 5/14551* (2013.01); *A61B 5/6824* (2013.01); *A61B 5/7278* (2013.01); *A61B 5/742* (2013.01); *A61B 5/02416* (2013.01)

(58) Field of Classification Search
CPC .............. A61B 5/14551; A61B 5/0022; A61B 5/02416; A61B 5/14552; A61B 2562/04; A61B 2562/06
See application file for complete search history.

(56) References Cited

U.S. PATENT DOCUMENTS

| | | | |
|---|---|---|---|
| 4,367,752 A | 1/1983 | Jimenez et al. | |
| 4,771,792 A | 9/1988 | Seale | |
| 4,781,195 A | 11/1988 | Martin | |
| 4,846,183 A | 7/1989 | Martin | |
| 4,960,126 A | 10/1990 | Conlon et al. | |
| 5,036,856 A | 8/1991 | Thornton | |
| 5,101,831 A | 4/1992 | Koyama et al. | |
| 5,301,154 A | 4/1994 | Suga | |
| 5,318,597 A | 6/1994 | Hauck et al. | |
| 5,490,523 A | 2/1996 | Isaacson et al. | |
| 5,513,649 A | 5/1996 | Gevins et al. | |
| 5,734,625 A | 3/1998 | Kondo | |
| 5,738,104 A | 4/1998 | Lo et al. | |
| 5,830,137 A | 11/1998 | Scharf | |
| 5,954,644 A | 9/1999 | Dettling et al. | |
| 6,076,015 A | 6/2000 | Hartley et al. | |
| 6,099,478 A | 8/2000 | Aoshima et al. | |
| 6,131,076 A | 10/2000 | Stephan et al. | |
| 6,241,684 B1 | 6/2001 | Amano et al. | |
| 6,289,230 B1 | 9/2001 | Chaiken et al. | |
| 6,307,576 B1 | 10/2001 | Rosenfeld | |
| 6,360,113 B1 | 3/2002 | Dettling | |
| 6,402,690 B1 | 6/2002 | Rhee et al. | |
| 6,418,394 B1 | 7/2002 | Puolakanaho et al. | |
| 6,583,369 B2 | 6/2003 | Montagnino et al. | |
| 6,585,622 B1 | 7/2003 | Shum et al. | |
| 6,731,967 B1 | 5/2004 | Turcott | |
| 6,882,955 B1 | 4/2005 | Ohlenbusch et al. | |
| 6,959,259 B2 | 10/2005 | Vock et al. | |
| 6,997,882 B1 | 2/2006 | Parker et al. | |
| 7,020,508 B2 | 3/2006 | Stivoric et al. | |
| 7,153,262 B2 | 12/2006 | Stivoric et al. | |
| 7,171,331 B2 | 1/2007 | Vock et al. | |
| 7,252,639 B2 | 8/2007 | Kimura et al. | |
| 7,285,090 B2 | 10/2007 | Stivoric et al. | |
| 7,334,472 B2 | 2/2008 | Seo et al. | |
| 7,539,532 B2 | 5/2009 | Tran | |
| 7,579,946 B2 | 8/2009 | Case, Jr. | |
| 7,720,306 B2 | 5/2010 | Gardiner et al. | |
| 7,909,768 B1 | 3/2011 | Turcott | |
| 7,993,276 B2 | 8/2011 | Nazarian et al. | |
| 8,040,758 B1 | 10/2011 | Dickinson | |
| 8,073,707 B2 | 12/2011 | Teller et al. | |
| 8,109,858 B2 | 2/2012 | Redmann | |
| 8,140,143 B2 | 3/2012 | Picard et al. | |
| 8,152,745 B2 | 4/2012 | Smith et al. | |
| 8,157,731 B2 | 4/2012 | Teller et al. | |
| 8,172,761 B1 | 5/2012 | Rulkov et al. | |
| 8,199,126 B1 | 6/2012 | Taubman | |
| 8,211,503 B2 | 7/2012 | Tsao et al. | |
| 8,346,328 B2 | 1/2013 | Mannheimer et al. | |
| 8,386,042 B2 | 2/2013 | Yudovsky et al. | |
| 8,398,546 B2 | 3/2013 | Pacione et al. | |
| 8,444,578 B2 | 5/2013 | Bourget et al. | |
| 8,446,275 B2 | 5/2013 | Utter, II | |
| 8,475,367 B1 | 7/2013 | Yuen et al. | |
| 8,579,827 B1 | 11/2013 | Rulkov et al. | |
| 8,641,612 B2 | 2/2014 | Teller et al. | |
| 8,742,325 B1 | 6/2014 | Droz et al. | |
| 8,792,981 B2 | 7/2014 | Yudovsky et al. | |
| 8,868,377 B2 | 10/2014 | Yuen et al. | |
| 8,909,543 B2 | 12/2014 | Tropper et al. | |
| 8,920,332 B2 | 12/2014 | Hong et al. | |
| 8,936,552 B2 | 1/2015 | Kateraas et al. | |
| 8,945,017 B2 | 2/2015 | Venkatraman et al. | |
| 8,948,832 B2 | 2/2015 | Hong et al. | |
| 8,954,135 B2 | 2/2015 | Yuen et al. | |
| 8,956,303 B2 | 2/2015 | Hong et al. | |
| 8,961,413 B2 | 2/2015 | Teller et al. | |
| 8,998,815 B2 | 4/2015 | Venkatraman et al. | |
| 9,005,129 B2 | 4/2015 | Venkatraman et al. | |
| 9,014,790 B2 | 4/2015 | Richards et al. | |
| 9,031,812 B2 | 5/2015 | Roberts et al. | |
| 9,042,971 B2 | 5/2015 | Brumback et al. | |
| 9,044,149 B2 | 6/2015 | Richards et al. | |
| 9,044,150 B2 | 6/2015 | Brumback et al. | |
| 9,049,998 B2 | 6/2015 | Brumback et al. | |
| 9,089,760 B2 | 7/2015 | Tropper et al. | |
| 9,113,794 B2 | 8/2015 | Hong et al. | |
| 9,113,795 B2 | 8/2015 | Hong et al. | |
| 9,226,663 B2 | 1/2016 | Fei | |
| 9,237,855 B2 | 1/2016 | Hong et al. | |
| 9,282,902 B2 | 3/2016 | Richards et al. | |
| 9,307,917 B2 | 4/2016 | Hong et al. | |
| 9,314,166 B1 | 4/2016 | Brady et al. | |
| 9,314,197 B2 | 4/2016 | Eisen et al. | |
| 9,392,946 B1 | 7/2016 | Sarantos et al. | |
| 9,402,552 B2 | 8/2016 | Richards et al. | |
| 9,456,787 B2 | 10/2016 | Venkatraman et al. | |
| 9,662,053 B2 | 5/2017 | Richards et al. | |
| 9,775,548 B2 | 10/2017 | Sarantos et al. | |
| 10,178,973 B2 | 1/2019 | Venkatraman et al. | |
| 10,216,893 B2 | 2/2019 | Hong et al. | |
| 10,216,894 B2 | 2/2019 | Hong et al. | |
| 10,381,109 B2 | 8/2019 | Hong et al. | |
| 10,433,739 B2 | 10/2019 | Weekly et al. | |
| 10,512,407 B2 | 12/2019 | Richards et al. | |
| 10,568,525 B1 | 2/2020 | Wu et al. | |
| 2001/0000445 A1 | 11/2001 | Mault | |
| 2002/0077536 A1 | 6/2002 | Diab et al. | |
| 2002/0091329 A1 | 7/2002 | Heikkila et al. | |
| 2002/0139936 A1 | 10/2002 | Dumas | |
| 2003/0107487 A1 | 6/2003 | Korman et al. | |
| 2003/0128867 A1 | 7/2003 | Bennett | |
| 2003/0163710 A1 | 8/2003 | Ortiz et al. | |
| 2003/0229276 A1 | 12/2003 | Sarussi et al. | |
| 2004/0171969 A1 | 9/2004 | Socci et al. | |
| 2004/0190085 A1 | 9/2004 | Silverbrook et al. | |
| 2004/0236227 A1 | 11/2004 | Gueissaz | |
| 2005/0020927 A1 | 1/2005 | Blondeau et al. | |
| 2005/0054940 A1 | 3/2005 | Almen | |
| 2005/0245793 A1 | 11/2005 | Hilton et al. | |
| 2005/0253047 A1 | 11/2005 | Maegawa et al. | |
| 2006/0052727 A1 | 3/2006 | Palestrant | |
| 2006/0195020 A1 | 8/2006 | Martin et al. | |
| 2007/0213020 A1 | 9/2007 | Novac | |
| 2007/0219059 A1 | 9/2007 | Schwartz et al. | |
| 2007/0265533 A1 | 11/2007 | Tran | |
| 2008/0039729 A1 | 2/2008 | Cho et al. | |
| 2008/0088467 A1* | 4/2008 | Al-Ali | A61B 5/14552 340/679 |
| 2008/0097221 A1 | 4/2008 | Florian | |
| 2008/0214360 A1 | 9/2008 | Stirling et al. | |
| 2008/0214903 A1 | 9/2008 | Orbach | |
| 2009/0012433 A1 | 1/2009 | Fernstrom et al. | |
| 2009/0132197 A1 | 5/2009 | Rubin et al. | |
| 2009/0143655 A1 | 6/2009 | Shani | |
| 2009/0163783 A1 | 6/2009 | Mannheimer et al. | |
| 2009/0216499 A1 | 8/2009 | Tobola et al. | |
| 2009/0292332 A1 | 11/2009 | Li et al. | |
| 2009/0318779 A1 | 12/2009 | Tran | |
| 2010/0026995 A1 | 2/2010 | Merritt et al. | |
| 2010/0063365 A1 | 3/2010 | Pisani et al. | |

(56) References Cited

U.S. PATENT DOCUMENTS

| | | |
|---|---|---|
| 2010/0079291 A1 | 4/2010 | Kroll et al. |
| 2010/0106044 A1 | 4/2010 | Linderman |
| 2010/0113948 A1 | 5/2010 | Yang et al. |
| 2010/0152600 A1 | 6/2010 | Droitcour et al. |
| 2010/0204550 A1 | 8/2010 | Heneghan et al. |
| 2010/0240972 A1 | 9/2010 | Neal |
| 2010/0249633 A1 | 9/2010 | Droitcour et al. |
| 2010/0274100 A1 | 10/2010 | Behar et al. |
| 2010/0292568 A1 | 11/2010 | Droitcour et al. |
| 2010/0298650 A1 | 11/2010 | Moon et al. |
| 2010/0298651 A1 | 11/2010 | Moon et al. |
| 2010/0298653 A1 | 11/2010 | McCombie et al. |
| 2010/0298661 A1 | 11/2010 | McCombie et al. |
| 2010/0331145 A1 | 12/2010 | Lakovic et al. |
| 2010/0331657 A1 | 12/2010 | Mensinger et al. |
| 2011/0009727 A1 | 1/2011 | Mensinger et al. |
| 2011/0032105 A1 | 2/2011 | Hoffman et al. |
| 2011/0066010 A1 | 3/2011 | Moon et al. |
| 2011/0112442 A1 | 5/2011 | Meger et al. |
| 2011/0118621 A1 | 5/2011 | Chu |
| 2011/0237911 A1 | 9/2011 | Lamego et al. |
| 2011/0237912 A1 | 9/2011 | Couronne et al. |
| 2011/0263950 A1 | 10/2011 | Larson et al. |
| 2011/0276304 A1 | 11/2011 | Yin et al. |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0123232 A1 | 5/2012 | Najarian et al. |
| 2012/0140233 A1 | 6/2012 | Rockwell et al. |
| 2012/0143067 A1 | 6/2012 | Watson et al. |
| 2012/0150074 A1 | 6/2012 | Yanev et al. |
| 2012/0172733 A1 | 7/2012 | Park |
| 2012/0226471 A1 | 9/2012 | Yuen et al. |
| 2012/0226472 A1 | 9/2012 | Yuen et al. |
| 2012/0232432 A1 | 9/2012 | Kahn et al. |
| 2012/0245439 A1 | 9/2012 | Andre et al. |
| 2012/0253486 A1 | 10/2012 | Niemimaki |
| 2012/0255875 A1 | 10/2012 | Vicente et al. |
| 2012/0271180 A1 | 10/2012 | Ren et al. |
| 2012/0274508 A1 | 11/2012 | Brown et al. |
| 2012/0316471 A1 | 12/2012 | Rahman et al. |
| 2013/0009779 A1 | 1/2013 | Wittling et al. |
| 2013/0053661 A1 | 2/2013 | Alberth et al. |
| 2013/0073254 A1 | 3/2013 | Yuen et al. |
| 2013/0073255 A1 | 3/2013 | Yuen et al. |
| 2013/0077823 A1 | 3/2013 | Mestha et al. |
| 2013/0077826 A1 | 3/2013 | Cowperthwaite et al. |
| 2013/0079607 A1 | 3/2013 | Gareau et al. |
| 2013/0080113 A1 | 3/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0173171 A1 | 7/2013 | Drysdale et al. |
| 2013/0191034 A1 | 7/2013 | Weast et al. |
| 2013/0211265 A1 | 8/2013 | Bedingham et al. |
| 2013/0218053 A1 | 8/2013 | Kaiser et al. |
| 2013/0245436 A1 | 9/2013 | Tupin, Jr. et al. |
| 2013/0261415 A1 | 10/2013 | Ashe et al. |
| 2014/0039284 A1 | 2/2014 | Niwayama et al. |
| 2014/0073486 A1 | 3/2014 | Ahmed et al. |
| 2014/0074431 A1 | 3/2014 | Modi |
| 2014/0099614 A1 | 4/2014 | Hu et al. |
| 2014/0107493 A1 | 4/2014 | Yuen et al. |
| 2014/0135612 A1 | 5/2014 | Yuen et al. |
| 2014/0135631 A1 | 5/2014 | Brumback et al. |
| 2014/0142403 A1 | 5/2014 | Brumback et al. |
| 2014/0228649 A1 | 8/2014 | Rayner |
| 2014/0241626 A1 | 8/2014 | Sull et al. |
| 2014/0275821 A1 | 9/2014 | Beckman |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278139 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0303523 A1 | 10/2014 | Hong et al. |
| 2014/0378786 A1 | 12/2014 | Hong et al. |
| 2014/0378787 A1 | 12/2014 | Brumback et al. |
| 2014/0378844 A1 | 12/2014 | Fei |
| 2014/0378872 A1 | 12/2014 | Hong et al. |
| 2015/0025393 A1 | 1/2015 | Hong et al. |
| 2015/0025394 A1 | 1/2015 | Hong et al. |
| 2015/0173631 A1 | 6/2015 | Richards et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0223708 A1 | 8/2015 | Richards et al. |
| 2015/0230743 A1 | 8/2015 | Silveira et al. |
| 2015/0230761 A1 | 8/2015 | Brumback et al. |
| 2015/0282713 A1 | 10/2015 | Fei |
| 2015/0351646 A1 | 12/2015 | Cervini |
| 2015/0366469 A1 | 12/2015 | Harris et al. |
| 2015/0366504 A1 | 12/2015 | Connor et al. |
| 2016/0034634 A9 | 2/2016 | Hong et al. |
| 2016/0058309 A1 | 3/2016 | Han |
| 2016/0058312 A1 | 3/2016 | Han et al. |
| 2016/0113585 A1 | 4/2016 | Uedaira et al. |
| 2016/0183818 A1 | 6/2016 | Richards et al. |
| 2016/0302706 A1 | 10/2016 | Richards et al. |
| 2016/0345881 A1 | 12/2016 | Sarantos et al. |
| 2017/0020659 A1 | 1/2017 | Hyde et al. |
| 2017/0027523 A1 | 2/2017 | Venkatraman et al. |
| 2017/0067778 A1* | 3/2017 | Sugi .................. G01S 17/88 |
| 2017/0164848 A1 | 6/2017 | Nadeau et al. |
| 2017/0311825 A1 | 11/2017 | Weekly et al. |
| 2018/0108802 A1 | 4/2018 | Chen |
| 2019/0082985 A1 | 3/2019 | Hong et al. |
| 2019/0385708 A1 | 12/2019 | Hong et al. |
| 2020/0138309 A1 | 5/2020 | Weekly et al. |

FOREIGN PATENT DOCUMENTS

| | | |
|---|---|---|
| CN | 101039617 A | 9/2007 |
| CN | 100362963 C | 1/2008 |
| CN | 101615098 A | 12/2009 |
| CN | 101730503 | 6/2010 |
| CN | 101742981 A | 6/2010 |
| CN | 101940476 A | 1/2011 |
| CN | 10208811 A | 4/2011 |
| CN | 202069586 U | 12/2011 |
| CN | 10238313 A | 3/2012 |
| CN | 102551686 A | 7/2012 |
| CN | 102750015 A | 10/2012 |
| CN | 102781310 A | 11/2012 |
| CN | 103093420 A | 5/2013 |
| CN | 104379055 A | 2/2015 |
| EP | 1 297 784 A1 | 4/2003 |
| EP | 1 586 353 A1 | 10/2005 |
| EP | 1 721 237 | 8/2012 |
| JP | 2010-169410 A | 5/2010 |
| WO | WO 2006/044677 A1 | 4/2006 |
| WO | WO 2014/091424 A2 | 6/2014 |
| WO | WO 2014/091424 A3 | 6/2014 |
| WO | WO 2017190051 | 11/2017 |

OTHER PUBLICATIONS

U.S. Notice of Allowance, dated Nov. 19, 2014, issued in U.S. Appl. No. 13/924,784.

U.S. Office Action, dated October 22, 2014, issued in U.S. Appl. No. 14/290,884.

U.S. Notice of Allowance, dated Feb. 6, 2015, issued in U.S. Appl. No. 14/290,884.

U.S. Office Action, dated Jun. 22, 2015, issued in U.S. Appl. No. 14/693,710.

(56) References Cited

OTHER PUBLICATIONS

U.S. Notice of Allowance, dated Jul. 27, 2015, issued in U.S. Appl. No. 14/693,710.
U.S. Notice of Allowance, dated Apr. 15, 2016, issued in U.S. Appl. No. 14/954,753.
U.S. Office Action, dated Oct. 26, 2016, issued in U.S. Appl. No. 15/195,911.
U.S. Notice of Allowance, dated Jan. 23, 2017, issued in U.S. Appl. No. 15/195,911.
U.S. Notice of Allowance, dated Sep. 23, 2014, issued in U.S. Appl. No. 14/292,669.
U.S. Notice of Allowance (Corrected Notice of Allowability), dated Oct. 14, 2014, issued in U.S. Appl. No. 14/292,669.
U.S. Notice of Allowance (Corrected Notice of Allowability), dated Dec. 31, 2014, issued in U.S. Appl. No. 14/292,669.
U.S. Notice of Allowance, dated Oct. 14, 2014, issued in U.S. Appl. No. 14/295,144.
U.S. Notice of Allowance, dated Dec. 3, 2014, issued in U.S. Appl. No. 14/295,144.
U.S. Notice of Allowance, dated Sep. 26, 2014, issued in U.S. Appl. No. 14/295,158.
U.S. Notice of Allowance (Corrected Notice of Allowability), dated Dec. 31, 2014, issued in U.S. Appl. No. 14/295,158.
U.S. Office Action, dated Jan. 23, 2015, issued in U.S. Appl. No. 14/507,184.
U.S. Final Office Action, dated May 11, 2015, issued in U.S. Appl. No. 14/507,184.
U.S. Notice of Allowance, dated Aug. 11, 2015, issued in U.S. Appl. No. 14/507,184.
U.S. Notice of Allowance (Corrected Notice of Allowability), dated Dec. 18, 2015, issued in U.S. Appl. No. 14/507,184.
U.S. Office Action, dated Jan. 26, 2015, issued in U.S. Appl. No. 14/295,161.
U.S. Notice of Allowance, dated Apr. 14, 2015, issued in U.S. Appl. No. 14/295,161.
U.S. Notice of Allowance, dated July 28, 2015, issued in U.S. Appl. No. 14/295,161.
U.S. Office Action, dated May 11, 2015, issued in U.S. Appl. No. 14/673,630.
U.S. Notice of Allowance, dated Nov. 25, 2015, issued in U.S. Appl. No. 14/673,630.
U.S. Notice of Allowance (Corrected Notice of Allowability), dated Mar. 21, 2016, issued in U.S. Appl. No. 14/673,630.
U.S. Office Action, dated Jan. 27, 2015, issued in U.S. Appl. No. 14/507,173.
U.S. Notice of Allowance, dated Apr. 17, 2015, issued in U.S. Appl. No. 14/507,173.
U.S. Notice of Allowance (Corrected Notice of Allowability), dated Jul. 16, 2015, issued in U.S. Appl. No. 14/507,173.
U.S. Office Action, dated Jun. 8, 2015, issued in U.S. Appl. No. 14/673,634.
U.S. Final Office Action, dated Nov. 4, 2015, issued in U.S. Appl. No. 14/673,634.
U.S. Office Action, dated Jul. 13, 2016, issued in U.S. Appl. No. 14/673,634.
U.S. Office Action, dated Feb. 9, 2017, issued in U.S. Appl. No. 14/673,634.
U.S. Final Office Action, dated Aug. 9, 2017, issued in U.S. Appl. No. 14/673,634.
U.S. Office Action, dated Mar. 27, 2018, issued in U.S. Appl. No. 14/673,634.
U.S. Office Action, dated Aug. 5, 2014, issued in U.S. Appl. No. 14/292,673.
U.S. Notice of Allowance, dated Dec. 8, 2014, issued in U.S. Appl. No. 14/292,673.
U.S. Notice of Allowance (Corrected Notice of Allowability), dated Mar. 5, 2015, issued in U.S. Appl. No. 14/292,673.
U.S. Office Action, dated Sep. 18, 2014, issued in U.S. Appl. No. 14/295,059.
U.S. Notice of Allowance, dated Jan. 28, 2015, issued in U.S. Appl. No. 14/295,059.
U.S. Notice of Allowance (Corrected Notice of Allowability), dated Mar. 11, 2015, issued in U.S. Appl. No. 14/295,059.
U.S. Office Action, dated Dec. 24, 2014, issued in U.S. Appl. No. 14/295,076.
U.S. Final Office Action, dated April 15, 2015, issued in U.S. Appl. No. 14/295,076.
U.S. Office Action, dated Oct. 22, 2015, issued in U.S. Appl. No. 14/295,076.
U.S. Notice of Allowance, dated May 24, 2016, issued in U.S. Appl. No. 14/295,076.
U.S. Office Action, dated Jan. 12, 2018, issued in U.S. Appl. No. 15/246,387.
U.S. Notice of Allowance, dated Aug. 29, 2018, issued in U.S. Appl. No. 15/246,387.
U.S. Office Action, dated Jul. 31, 2014, issued in U.S. Appl. No. 14/295,122.
U.S. Notice of Allowance, dated Nov. 24, 2014, issued in U.S. Appl. No. 14/295,122.
U.S. Notice of Allowance (Corrected Notice of Allowability), dated Jan. 5, 2015, issued in U.S. Appl. No. 14/295,122.
U.S. Office Action dated Dec. 22, 2016, issued in U.S. Appl. No. 14/599,039.
U.S. Final Office Action dated Aug. 3, 2017, issued in U.S. Appl. No. 14/599,039.
U.S. Office Action, dated Mar. 14, 2014, issued in U.S. Appl. No. 14/154,009.
U.S. Office Action, dated Sep. 29, 2014, issued in U.S. Appl. No. 14/154,009.
U.S. Notice of Allowance, dated Jan. 21, 2015, issued in U.S. Appl. No. 14/154,009.
U.S. Office Action, dated Nov. 25, 2014, issued in U.S. Appl. No. 14/154,019.
U.S. Notice of Allowance, dated Mar. 20, 2015, issued in U.S. Appl. No. 14/154,019.
U.S. Notice of Allowance (Corrected Notice of Allowability), dated May 14, 2015, issued in U.S. Appl. No. 14/154,019.
U.S. Office Action, dated Jul. 24, 2018, issued in U.S. Appl. No. 14/696,256.
U.S. Final Office Action, dated Feb. 26, 2019, issued in U.S. Appl. No. 14/696,256.
U.S. Office Action, dated Feb. 19, 2020, issued in U.S. Appl. No. 14/696,256.
U.S. Office Action, dated Dec. 10, 2014, issued in U.S. Appl. No. 14/484,104.
U.S. Notice of Allowance, dated March 19, 2015, issued in U.S. Appl. No. 14/484,104.
U.S. Notice of Allowance (Corrected Notice of Allowability), dated May 6, 2015, issued in U.S. Appl. No. 14/484,104.
U.S. Office Action, dated Dec. 4, 2014, issued in U.S. Appl. No. 14/216,743.
U.S. Final Office Action, dated Apr. 8, 2015, issued in U.S. Appl. No. 14/216,743.
U.S. Office Action, dated Oct. 2, 2015, issued in U.S. Appl. No. 14/216,743.
U.S. Final Office Action, dated Feb. 8, 2016, issued in U.S. Appl. No. 14/216,743.
U.S. Office Action, dated May 16, 2016, issued in U.S. Appl. No. 14/216,743.
U.S. Office Action, dated Jan. 13, 2017, issued in U.S. Appl. No. 14/216,743.
US Examiner's Answer to Appeal Brief before the Patent Trial and Appeal Board [in response to the appeal brief filed Sep. 12, 2017 appealing from the Office action dated Jan. 3, 2017], dated Nov. 30, 2017, issued in U.S. Appl. No. 14/216,743.
US Patent Trial and Appeal Board's Decision on Appeal, dated Oct. 9, 2018, issued in U.S. Appl. No. 14/216,743.
U.S. Notice of Allowance, dated Dec. 17, 2018, issued in U.S. Appl. No. 14/216,743.
U.S. Office Action, dated Mar. 12, 2015, issued in U.S. Appl. No. 14/481,020.

(56) References Cited

OTHER PUBLICATIONS

U.S. Final Office Action, dated Jul. 7, 2015, issued in U.S. Appl. No. 14/481,020.
U.S. Office Action, dated Oct. 27, 2015, issued in U.S. Appl. No. 14/481,020.
U.S. Final Office Action, dated May 13, 2016, issued in U.S. Appl. No. 14/481,020.
US Examiner's Answer to Appeal Brief before the Patent Trial and Appeal Board [in response to the appeal brief filed Dec. 9, 16 appealing from the Office action dated May 13, 16], dated Jan. 23, 2017, issued in U.S. Appl. No. 14/481,020.
US Patent Trial and Appeal Board's Decision on Appeal, dated Sep. 14, 2018, issued in U.S. Appl. No. 14/481,020.
U.S. Notice of Allowance, dated Nov. 29, 2018, issued in U.S. Appl. No. 14/481,020.
U.S. Office Action, dated August 22, 2014, issued in U.S. Appl. No. 14/250,256.
U.S. Final Office Action, dated Nov. 21, 2014, issued in U.S. Appl. No. 14/250,256.
U.S. Office Action, dated Jul. 8, 2015, issued in U.S. Appl. No. 14/250,256.
U.S. Final Office Action, dated Oct. 23, 2015, issued in U.S. Appl. No. 14/250,256.
U.S. Office Action, dated Mar. 17, 2016, issued in U.S. Appl. No. 14/250,256.
U.S. Final Office Action, dated Jun. 29, 2016, issued in U.S. Appl. No. 14/250,256.
U.S. Office Action, dated Jan. 9, 2017, issued in U.S. Appl. No. 14/250,256.
US Examiner's Answer to the Appeal Brief before the Patent Trial and Appeal Board [in response to the appeal brief filed Jul. 11, 2017 appealing from the Office action dated Jan. 9, 2017], dated Aug. 24, 2017, issued in U.S. Appl. No. 14/250,256.
US Patent Trial and Appeal Board's Decision on Appeal, dated Oct. 9, 2018, issued in U.S. Appl. No. 14/250,256.
U.S. Notice of Allowance, dated Mar. 29, 2019, issued in U.S. Appl. No. 14/250,256.
U.S. Office Action, dated Oct. 7, 2014, issued in U.S. Appl. No. 14/481,762.
U.S. Final Office Action, dated Dec. 19, 2014, issued in U.S. Appl. No. 14/481,762.
U.S. Office Action, dated Jul. 7, 2015, issued in U.S. Appl. No. 14/481,762.
U.S. Final Office Action, dated Nov. 5, 2015, issued in U.S. Appl. No. 14/481,762.
U.S. Office Action, dated May 11, 2016, issued in U.S. Appl. No. 14/481,762.
U.S. Final Office Action, dated Oct. 19, 2016, issued in U.S. Appl. No. 14/481,762.
U.S. Office Action, dated Apr. 12, 2017, issued in U.S. Appl. No. 14/481,762.
U.S. Office Action, dated Nov. 19, 2015, issued in U.S. Appl. No. 14/724,750.
U.S. Notice of Allowance, dated Mar. 8, 2016, issued in U.S. Appl. No. 14/724,750.
U.S. Office Action dated Sep. 8, 2016, issued in U.S. Appl. No. 15/192,447.
U.S. Final Office Action dated Feb. 7, 2017, issued in U.S. Appl. No. 15/192,447.
U.S. Notice of Allowance dated May 24, 2017, issued in U.S. Appl. No. 15/192,447.
U.S. Office Action dated Mar. 15, 2017, issued in U.S. Appl. No. 15/370,303.
U.S. Final Office Action dated Aug. 1, 2017, issued in U.S. Appl. No. 15/370,303.
U.S. Office Action dated Jan. 11, 2018, issued in U.S. Appl. No. 15/370,303.
U.S. Final Office Action dated Jul. 25, 2018, issued in U.S. Appl. No. 15/370,303.
U.S. Office Action dated May 24, 2019, issued in U.S. Appl. No. 15/370,303.
U.S. Office Action, dated Oct. 7, 2014, issued in U.S. Appl. No. 14/292,844.
U.S. Notice of Allowance, dated Feb. 9, 2015, issued in U.S. Appl. No. 14/292,844.
U.S. Office Action, dated Jul. 6, 2015, issued in U.S. Appl. No. 14/640,281.
U.S. Final Office Action, dated Nov. 12, 2015, issued in U.S. Appl. No. 14/640,281.
U.S. Office Action, dated Oct. 6, 2016, issued in U.S. Appl. No. 14/640,281.
U.S. Final Office Action, dated May 4, 2017, issued in U.S. Appl. No. 14/640,281.
U.S. Office Action, dated Jun. 29, 2018, issued in U.S. Appl. No. 14/640,281.
U.S. Final Office Action, dated Feb. 21, 2019, issued in U.S. Appl. No. 14/640,281.
U.S. Notice of Allowance, dated Aug. 2, 2019, issued in U.S. Appl. No. 14/640,281.
U.S. Office Action, dated May 30, 2019, issued in U.S. Appl. No. 15/376,542.
U.S. Notice of Allowance, dated Sep. 20, 2019, issued in U.S. Appl. No. 15/376,542.
U.S. Office Action, dated Mar. 11, 2019, issued in U.S. Appl. No. 15/582,240.
U.S. Notice of Allowance, dated June 14, 2019, issued in U.S. Appl. No. 15/582,240.
Chinese First Office Action dated Sep. 27, 2016 issued in Application No. CN 201410018701.8.
Chinese Second Office Action dated Jun. 13, 2017 issued in Application No. CN 201410018701.8.
Chinese First Office Action dated Aug. 7, 2015 issued in Application No. CN 201410243180.6.
Chinese First Office Action dated Sep. 2, 2016 issued in Application No. CN 201510745382.5.
Chinese Second Office Action dated Mar. 22, 2017 issued in Application No. CN 201510745382.5.
Chinese First Office Action dated Mar. 22, 2018 issued in Application No. CN 201610284612.7.
Chinese Second Office Action dated Nov. 6, 2018 issued in Application No. CN 201610284612.7.
Chinese First Office Action dated Aug. 3, 2016 issued in Application No. CN 201410243169.X.
Chinese Second Office Action dated Mar. 27, 2017 issued in Application No. CN 201410243169.X.
Chinese Third Office Action dated Sep. 28, 2017 issued in Application No. CN 201410243169.X.
Chinese First Office Action dated Sep. 26, 2016 issued in Application No. CN 201410243178.9.
Chinese Second Office Action dated Jun. 15, 2017 issued in Application No. CN 201410243178.9.
Chinese First Office Action dated Mar. 3, 2017 issued in Application No. CN 201610622453.7.
Chinese Second Office Action dated Sep. 19, 2017 issued in Application No. CN 201610622453.7.
Chinese Third Office Action dated Jan. 24, 2018 issued in Application No. CN 201610622453.7.
Chinese Fourth Office Action dated Jun. 1, 2018 issued in Application No. CN 201610622453.7.
Chinese First Office Action dated Jul. 13, 2017 issued in Application No. CN 201610621114.7.
Chinese Second Office Action dated Apr. 9, 2018 issued in Application No. CN 201610621114.7.
Chinese Third Office Action dated Sep. 14, 2018 issued in Application No. CN 201610621114.7.
Chinese First Office Action dated Jan. 14, 2019 issued in Application No. CN 201510117698.X.
Chinese Second Office Action dated Jun. 21, 2019 issued in Application No. CN 201510117698.X.
Chinese First Office Action dated May 13, 2020, issued in Application No. CN 201610377864.4.

(56) References Cited

OTHER PUBLICATIONS

Chinese First Office Action dated Jan. 22, 2020, issued in Application No. CN 201780033558.1.
European Extended Search Report dated Oct. 25, 2016 issued in Application No. EP 16 16 8661.3.
European Office Action dated Mar. 19, 2019 issued in Application No. EP 16 16 8661.3.
European Extended Search Report dated Sep. 9, 2019, issued in Application No. EP 17790575.9.
International Search Report and Written Opinion—PCT/US2017/030190—ISA/US—dated Jul. 7, 2017 (dated Jul. 7, 2017).
Litigation Document—"Complaint for Patent Infringement," filed Sep. 3, 2015, in U.S. District Court of Delaware (Court Docket No. 1: 15-cv-00775-RGA).
Litigation Document—"Report on the Filing or Determination of an Action Regarding a Patent or Trademark," filed Sep. 3, 2015, in U.S. District Court of Delaware (Court Docket No. 1: 15-cv-00775-RGA).
Litigation Document—"Complaint for Patent Infringement," filed Oct. 29, 2015, in U.S. District Court of Delaware (Court Docket No. 1:15-cv-00990-RGA) [Re: U.S. Pat. No. 8,868,377, U.S. Pat. No. 8,920,332, and U.S. Pat. No. 9,089,760].
Litigation Document—"Report on the Filing or Determination of an Action Regarding a Patent or Trademark," filed Oct. 29, 2015, in U.S. District Court of Delaware (Court Docket No. 1:15-cv-00990-RGA) [Re: U.S. Pat. No. 8,868,377, U.S. Pat. No. 8,920,332, and U.S. Pat. No. 9,089,760].
Litigation Document—"Order No. 24: Initial Determination Granting Respondents' Motion for Summary Determination of Invalidity under 35 U.S.C. § 101 with respect to all Three Asserted Patents and Terminating the Investigation in its Entirety," filed Jul. 19, 2016, in United States International Trade Commission, Washington, D.C. (Investigation No. 337-TA-973) [In the Matter of Certain Wearable Activity Tracking Devices, Systems, and Components Thereof].
Litigation Document—"Respondents' Opposition to Complainant's Petition for Review of the Initial Determination Granting Summary Determination that the Asserted Patents are Directed to Ineligible Subject Matter under 35 U.S.C. § 101," filed Aug. 8, 2016, in United States International Trade Commission, Washington, D.C. (Investigation No. 337-TA-973) (4446833v1/014972) [In the Matter of Certain Wearable Activity Tracking Devices, Systems, and Components Thereof].
Litigation Document—"Declaration of Majid Sarrafzadeh in Support of Complainant's Brief in Opposition to Respondents' Motion for Summary Determination that the Asserted Patents are Directed to Ineligible Subject Matter under 35 U.S.C. § 101," filed June 2, 2016, in United States International Trade Commission, Washington, D.C. (Investigation No. 37-TA-973) [In the Matter of Certain Wearable Activity Tracking Devices, Systems, and Components Thereof] [Exhibit 7].
Litigation Document—"Kiaei Declaration in Support of Complainant's Supplemental Brief Regarding Construction of "Operating the Heart Rate Monitor in a Worn Detection Mode" under 35 U.S.C. § 112(f)," filed Apr. 29, 2016, in United States International Trade Commission, Washington, D.C. (Investigation No. 37-TA-973) [In the Matter of Certain Wearable Activity Tracking Devices, Systems, and Components Thereof] [Exhibit 8].
Litigation Document—"Memorandum in Support of Respondents' Motion for Summary Determination that the Asserted Patents are Directed to Ineligible Subject Matter under 35 U.S.C. § 101," filed May 23, 2016, in United States International Trade Commission, Washington, D.C. (Investigation No. 337-TA-973) (44325007v1/014972) [In the Matter of Certain Wearable Activity Tracking Devices, Systems, and Components Thereof].
Litigation Document—"Grimes Declaration in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [In the Matter of Certain Wearable Activity Tracking Devices, Systems, and Components Thereof] [Exhibit 28].
Litigation Document—"Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 337-TA-973) [In the Matter of Certain Wearable Activity Tracking Devices, Systems, and Components Thereof].
Litigation Document—"Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [In the Matter of Certain Wearable Activity Tracking Devices, Systems, and Components Thereof].
Litigation Document—"Summary Pursuant to 19 C.F.R. § 210.43(b)(2) of Complainant's Petition for Review of the Initial Determination Granting Summary Determination that the Asserted Patents are Directed to Ineligible Subject Matter under 35 U.S.C. § 101," filed August 1, 2016, in United States International Trade Commission, Washington, D.C. (Investigation No. 337-TA-973) [In the Matter of Certain Wearable Activity Tracking Devices, Systems, and Components Thereof].
Litigation Document—"Notice of Commission Determination to Review an Initial Determination Granting Respondents' Motion for Summary Determination that Certain Asserted Claims are Directed to Ineligible Subject Matter under 35 U.S.C. § 101; and on Review to Remand the Investigation to the Presiding Administrative Law Judge," issued Sep. 7, 2016, in United States International Trade Commission, Washington, D.C. (Investigation No. 337-TA-973) [In the Matter of Certain Wearable Activity Tracking Devices, Systems, and Components Thereof].
U.S. Appl. No. 61/736,310, filed Dec. 12, 2012, William Ahmed et al., entitled "Fitness Monitoring Systems and Methods Based on Continuous Collection of Physiological Data," 61pp [Exhibit 4].
U.S. Appl. No. 61/696,525, filed Sep. 4, 2012, William Ahmed et al., entitled "Fitness Monitoring Systems and Methods Based on Continuous Collection of Physiological Data," 47pp [Exhibit 5].
Gasparrini et al. (2013) "Evaluation and Possible Improvements of the ANT Protocol for Home Heart Monitoring Applications," *IEEE*, 978-1-4673-2874-6/13, 7pp [Exhibit 6].
"UP3™, The world's most advanced tracker," (Oct. 14, 2015) *Jawbone*, 10pp [Exhibit 12].
"UP4™, A fitness tracker so advanced it pays," (Oct. 14, 2015) *Jawbone*, 12pp [Exhibit 13].
"User's Guide, MIO Drive+ Petite," User's guide and how-to videos available at www.mioglobal.com, 3pp [Exhibit 16].
"SOLO 915, Heart Rate + Calorie Monitor," (2009) *SPORTLINE®*, [retrieved on Oct. 15, 2010 at www.sportline.com] 25pp [Exhibit 17].
U.S. Notice of Allowance dated Oct. 14, 2014 issued in U.S. Appl. No. 14/295,144, 5pp [Exhibit 18].
"Health Touch™ Plus User Guide," (2011) *Timex Group USA, Inc.*, 12pp [Exhibit 18].
Czarnul, Pawel (Jun. 6-8, 2013) "Design of a Distributed System using Mobile Devices and Workflow Management for Measurement and Control of a Smart Home and Health," Sopot, Poland, *IEEE*, pp. 184-192, 10pp [Exhibit 19].
Rabinovich, Roberto A., and Louvaris, Zafeiris et al. (Feb. 8, 2013) "Validity of Physical Activity Monitors During Daily Life in Patients With COPD," *ERJ Express, European Respiratory Society*, 28pp [Exhibit 24].
Horvath et al. (2007) "The effect of pedometer position and normal gait asymmetry on step count accuracy," *Appl. Physiol. Nutr. Metab.*, 32:409-415, 8pp [Exhibit 32].
Graser et al. (2007) "Effects of Placement, Attachment, and Weight Classification on Pedometer Accuracy," *Journal of Physical Activity and Health*, 4(4):359-369, 13pp [Exhibit 33].
Vyas et al. (2012) "Machine Learning and Sensor Fusion for Estimating Continuous Energy Expenditure," *AI Magazine*, pp. 55-61, 13pp [Exhibit 42].

(56) References Cited

OTHER PUBLICATIONS

"New Lifestyles, NL-800 Activity Monitor, User's guide & record book," (2005), New Lifestyles, Inc., 37pp.

"StepWatch Step Activity Monitor, U.S. Pat. No. 5,485,402," (2001) StepWatch™, *Prosthetics Research Study*, 7pp.

Litigation Document—"Plaintiff's Original Complaint For Patent Infringement," filed Jan. 4, 2016, in U.S. District Court for the Eastern District of North Carolina (Court Docket No. 5:16-cv-00002-FL) [Re: U.S. Pat. No. 8,923,941, U.S. Pat. No. 8,886,269, U.S. Pat. No. 8,929,965 and U.S. Pat. No. 8,989,830], 11 pages.

Cooper, Daniel (Aug. 16, 2013) *Withings Pulse review*, http://www.engadget.com/2013/08/16/withings-pulse-revew/, 8 pages.

Dunn et al. (2007) "A Novel Ring Shaped Photodiode for Reflectance Pulse Oximetry in Wireless Applications," *IEEE Sensors Conference*, pp. 596-599.

Kim, D. et al. A Linear Transformation Approach for Estimating Pulse Arrival Time. Journal of Applied Mathematics. vol. 2012. Jan. 20, 2012. [Retrieve Jun. 19, 2017]. Retrieved from internet: <https://www.emis.de/journals/HOA/JAM/Volume2012/643653.pdf> pp. 1-12.

LifeTRNR, User Manual (2003, specific date unknown), NB new balance®, Implus Footcare, LLC, 3 pages.

Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.

"Withings pulse, Quick Installation Guide" (Jul. 24, 2013) Withings Pulse QIG, v 1.3, withings.com/pulse, 16 pages.

Zijlstra, Wiebren, (2004) "Assessment of spatio-temporal parameters during unconstrained walking," *Eur J Appl Physiol*, 92:39-44.

U.S. Appl. No. 14/214,655, filed Mar. 14, 2014, Hong et al.

* cited by examiner

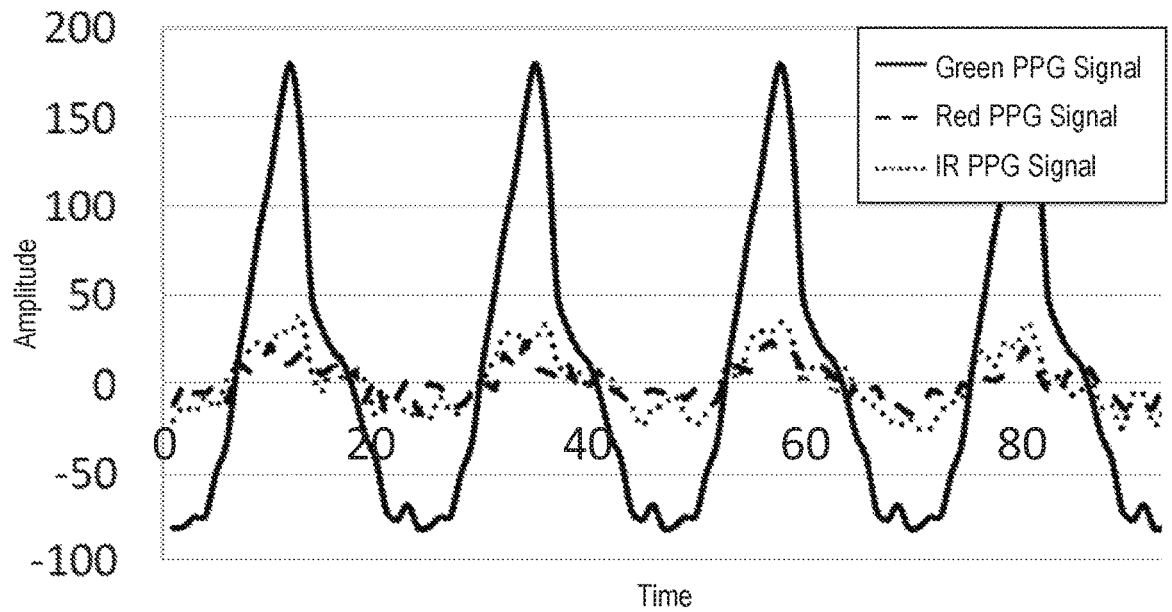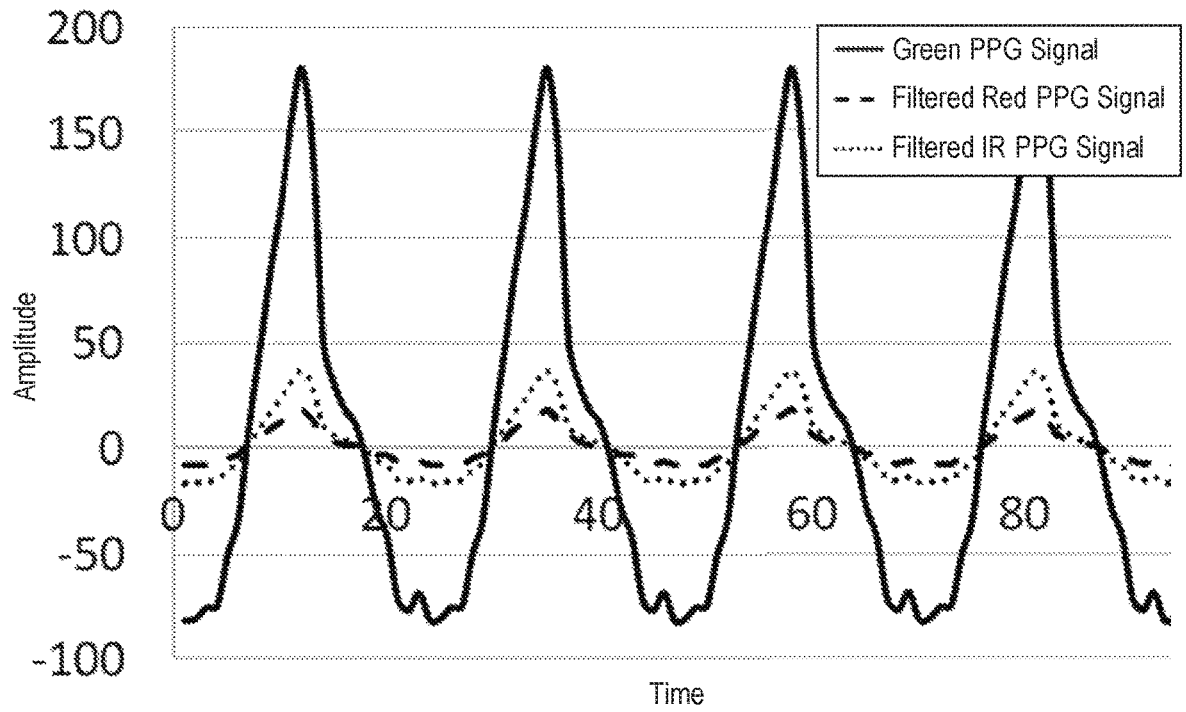
FIG. 7

MULTI-WAVELENGTH PULSE OXIMETRY

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD OF THE DISCLOSURE

The present disclosure generally relates to digital apparatus for reflectance-based pulse oximetry for noninvasively measuring oxygen saturation in blood vessels. The disclosure relates more specifically, in some cases, to techniques for removing noise from signals representing oxygen saturation that are received in a digital apparatus for reflectance-based pulse oximetry for noninvasively measuring oxygen saturation in blood vessels.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Blood oxygen saturation ($SpO_2$) refers to a fraction of oxygen-saturated hemoglobin relative to total hemoglobin in the blood. Decreased $SpO_2$ in the blood can lead to impaired mental function, or loss of consciousness, and may serve to indicate other serious health conditions, such as sleep apnea or cardiovascular disease. Therefore, accurately measuring $SpO_2$ is important in certain kinds of health monitoring.

Methods for measuring $SpO_2$ in the blood include invasive procedures, such as drawing blood, and noninvasive methods of monitoring $SpO_2$, such as through reflectance-based pulse oximetry. Reflectance-based pulse oximetry is a technique for monitoring $SpO_2$ by detecting the volumetric change of aerial blood vessels using photoplethysmography (PPG) with wavelengths in the red and infrared regions.

Pulse oximetry tends to be most effective when performed on areas of the body where blood vessels are close to the surface of the skin, such as the fingertip or forehead. While pulse oximetry tends to be most effective in these areas, devices for monitoring $SpO_2$ through pulse oximetry on the fingertip or forehead can be cumbersome. If a person wishes to monitor $SpO_2$ throughout the day, a device on the fingertip or forehead may be impractical.

In terms of wearing a device capable of measuring $SpO_2$, a user may prefer to wear such a device on other parts of the body, like on their wrist, which may be the case especially if the user is wearing the device for extended periods of time. However, measuring $SpO_2$ through pulse oximetry tends to be more difficult on these other body parts. Differences in skin morphology can cause light emitters to be less effective for some people than others. For instance, a person may have a mole or hair that covers a light emitter, thereby decreasing the quality of the signal received by the detector. The presence of cosmetic features such as tattoos also can affect signal quality. In addition, when blood vessels are further from the skin surface, or when there is low blood perfusion due to cool skin temperature, the presence of fatty tissue or other morphology such as cardiovascular disease, signal noise may decrease the quality of the received PPG signals.

SUMMARY

The appended claims may serve as a summary of the disclosure.

BRIEF DESCRIPTION OF THE DRAWINGS

In the drawings:

FIG. 7 is a two-part graph that illustrates example PPG signals before and after removal of noise based upon a heart rate signal.

DETAILED DESCRIPTION

Figure 1:
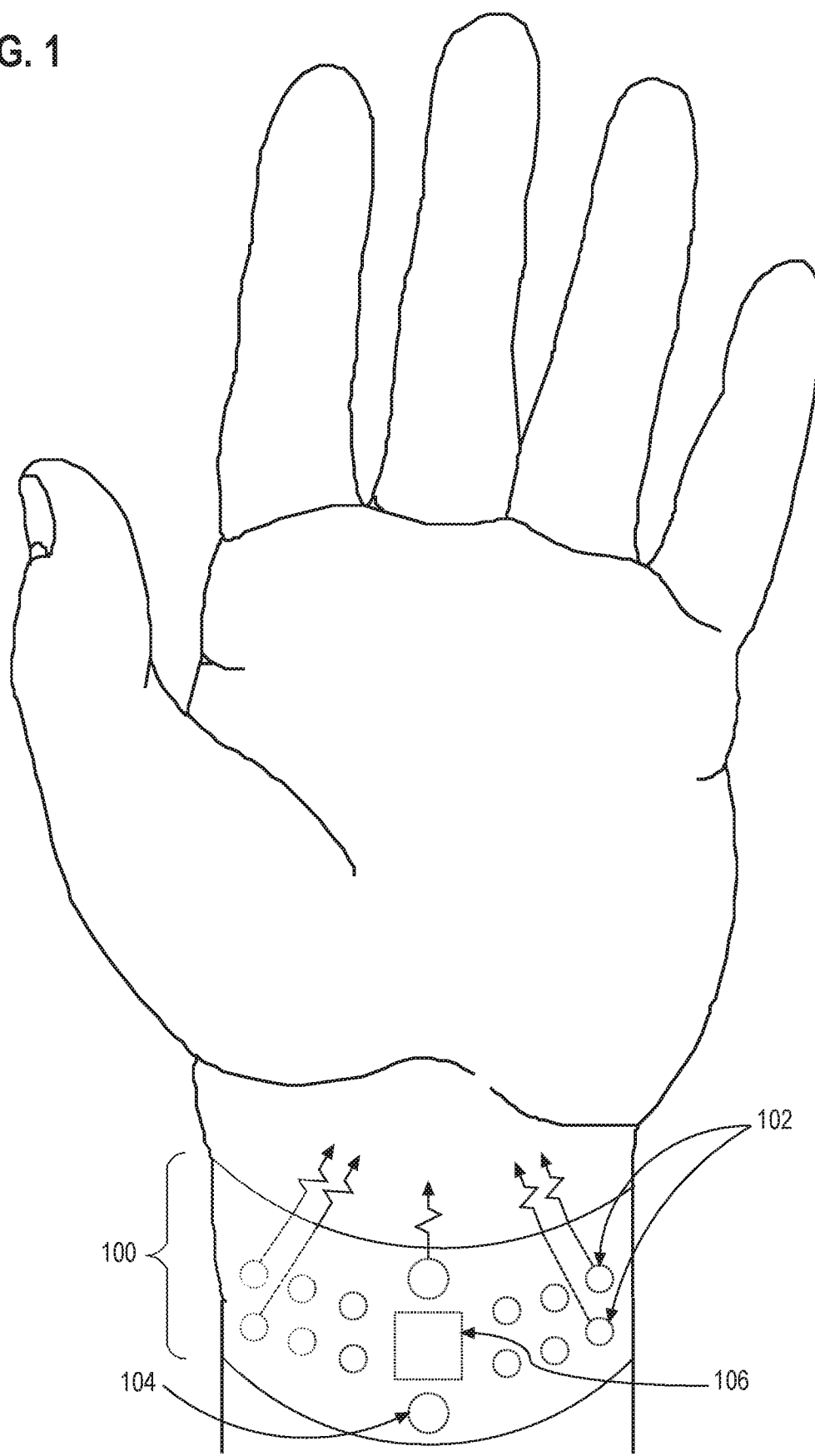
FIG. 1 illustrates a monitoring device worn by a user, in accordance with one example.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are described according to the following outline:

1. GENERAL OVERVIEW
2. EXAMPLE MONITORING DEVICE
3. NOISE REDUCTION THROUGH OTHER PPG SIGNALS
4. MULTIPLE EMITTERS WITH SPACING
5. OTHER ARRANGEMENTS OF LIGHT SOURCES AND/OR DETECTORS
6. IMPLEMENTATION EXAMPLE—HARDWARE OVERVIEW

1. General Overview

In one embodiment, a method for creating a blood oxygen saturation ($SpO_2$) value, the method comprises receiving one or more photoplethysmography (PPG) signals for $SpO_2$ detection from one or more PPG sensors; receiving one or more PPG signals for characterizing a heart rate from the one or more PPG sensors; using the one or more PPG signals for $SpO_2$ detection, forming one or more $SpO_2$ datasets wherein the $SpO_2$ datasets respectively comprise one or more noise components; removing the one or more noise components from the one or more $SpO_2$ datasets that are inconsistent with a feature of the one or more PPG signals characterizing the heart rate to produce one or more filtered $SpO_2$ datasets; and using the one or more filtered $SpO_2$ datasets, creating and storing the $SpO_2$ value.

In another embodiment, a monitoring device for creating a $SpO_2$ value comprises one or more processors coupled to electronic digital memory; in the memory, instructions which when executed by the one or more processors cause the one or more processors to perform: receive one or more PPG signals for $SpO_2$ detection from one or more PPG sensors; receive one or more PPG signals for characterizing a heart rate from the one or more PPG sensors; use the one or more PPG signals for $SpO_2$ detection, forming one or more $SpO_2$ datasets wherein the $SpO_2$ datasets respectively comprise one or more noise components; remove the one or more noise components from the one or more $SpO_2$ datasets that are inconsistent with a feature of the one or more PPG signals characterizing the heart rate, to produce one or more filtered $SpO_2$ datasets; and using the one or more filtered $SpO_2$ datasets, creating and storing a $SpO_2$ value.

In yet another embodiment, a data processing method comprises activating one or more first light sources from one or more PPG sensors; receiving one or more first PPG signals for $SpO_2$ detection from the one or more PPG sensors; determining that a quality of the one or more first PPG signals for $SpO_2$ detection is below a stored minimum signal value; based on the determining, activating one or more second light sources from the one or more PPG sensors; receiving one or more second PPG signals for $SpO_2$ detection from the one or more PPG sensors; and using the one or more second PPG signals, creating and storing a $SpO_2$ value.

In a further embodiment, a monitoring device comprises one or more processors coupled to electronic digital memory; and in the memory, instructions which when executed by the one or more processors cause the one or more processors to: activate one or more first light sources of a plurality of spaced apart light sources, receive one or more first PPG signals for blood oxygen saturation $SpO_2$ detection from one or more PPG sensors, determine that a quality of the one or more first PPG signals for $SpO_2$ detection is below a stored minimum signal value, based on the determining, activate one or more second light sources of the plurality of spaced apart light sources, receive one or more second PPG signals for $SpO_2$ detection from the one or more PPG sensors, determine that a quality of the one or more second PPG signals for $SpO_2$ detection is above the stored minimum signal value, and using the one or more second PPG signals, create and store a $SpO_2$ value.

In yet another embodiment, a monitoring device comprises an electronic digital microprocessor coupled to electronic digital memory; one or more detectors on a substrate and coupled to the microprocessor; one or more pairs of light sources that are laterally aligned on the substrate with respect to the one or more detectors; and one or more light sources that are longitudinally aligned on the substrate with respect to the one or more detectors.

In some embodiments, the execution of the method is performed using a monitoring device. Depending on embodiment, the monitoring device can be worn on a wrist (e.g., watch, band), finger (e.g., ring, clip), around a torso (e.g., chest strap), leg, head (e.g., clip on ear, headband, eye wear, and the like), or any other body part. In other embodiments, the techniques described herein may be performed using a server computer, desktop computer, or other computer that is not wearable, in which the computer receives a dataset and performs filtering and other processing operations as further described.

Various other aspects and features of different embodiments will become apparent from the description, drawings and claims.

2. Example Monitoring Device

Figure 2:
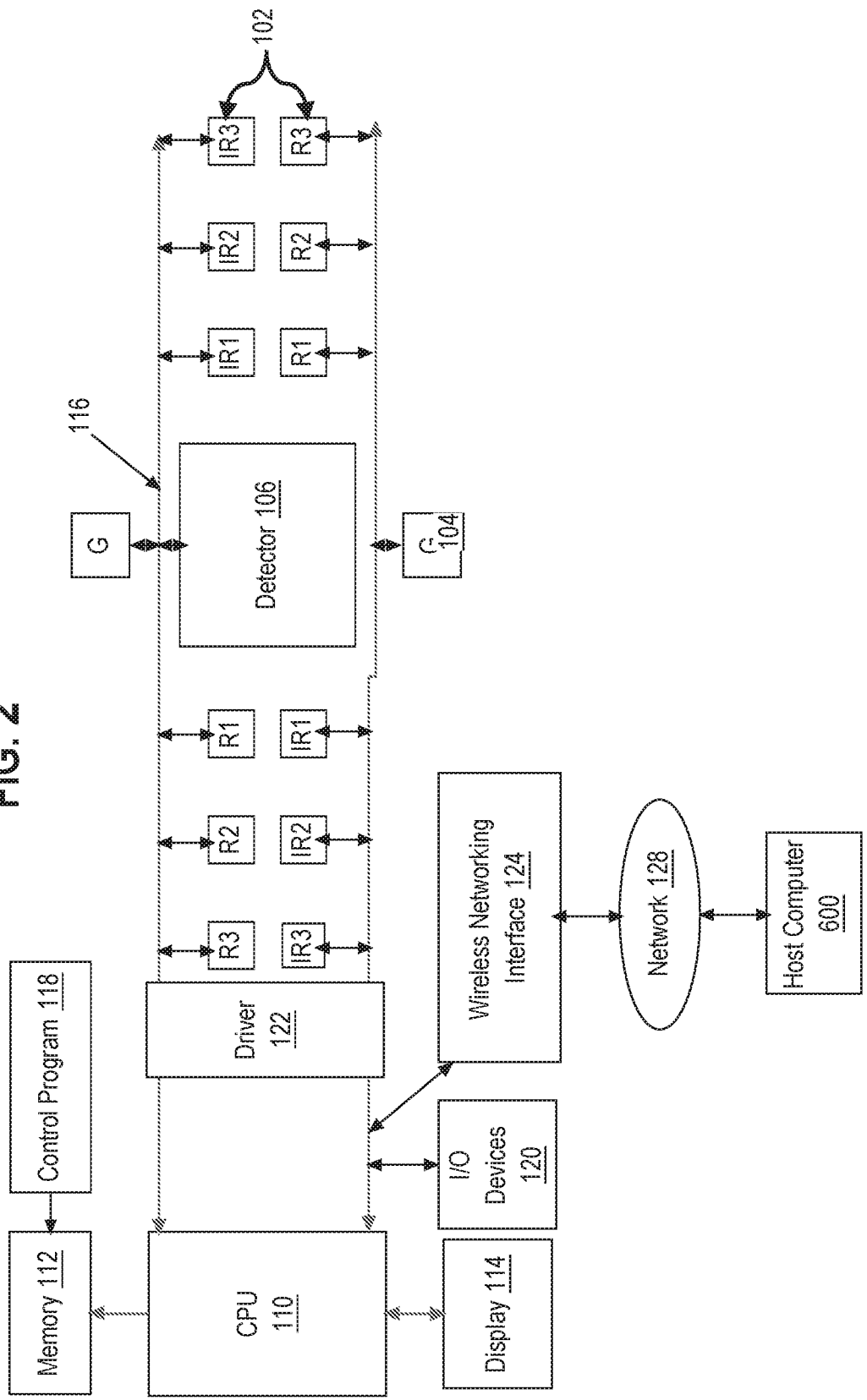
FIG. 2 illustrates an example hardware architecture of the monitoring device of FIG. 1, FIG. 5.
Figure 5:
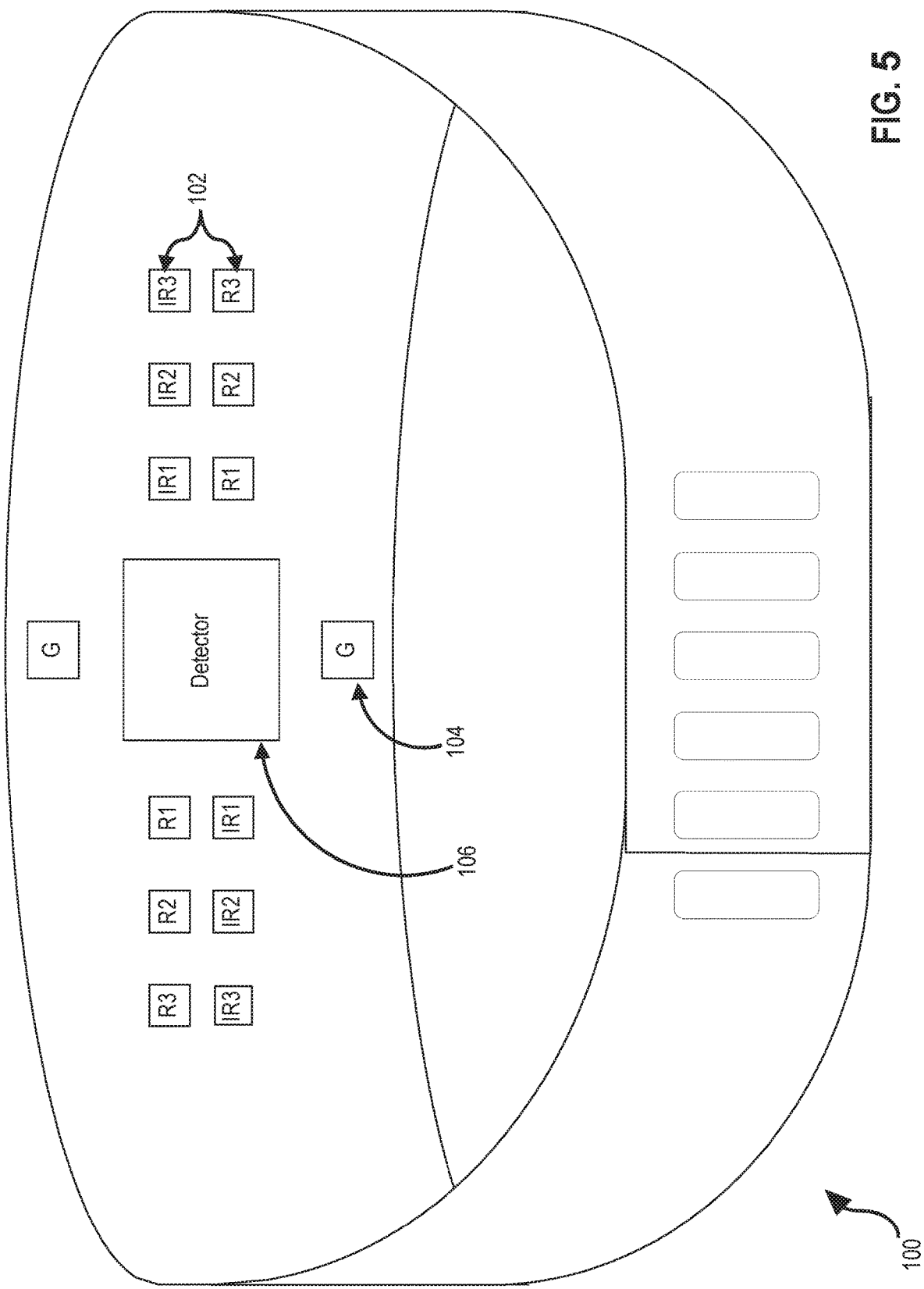
FIG. 5 illustrates a perspective view of a monitoring device, in accordance with one example.

FIG. 1 illustrates an example monitoring device in relation to a human hand. FIG. 2 illustrates an example hardware architecture of the monitoring device of FIG. 1, FIG. 5. FIG. 5 illustrates a perspective view of a monitoring device, in accordance with one example. For purposes of illustrating a clear example, FIG. 1 and other aspects of this disclosure describe a monitoring device that is configured for wearing on the wrist, but other embodiments may be implemented using monitoring devices that are wearable in other anatomical locations such as the fingertips, ankle, neck, upper arm, torso, leg and/or forehead.

In an embodiment, a monitoring device 100 comprises one or more pairs of light sources 102, one or more secondary light sources 104 and one or more detectors 106. For purposes of illustrating a clear example, FIG. 1 depicts light sources 102, 104 and detectors 106 in an enlarged form, and in practical embodiments, these elements may be implemented using miniature components that are smaller than shown in FIG. 1. In practice, the light sources 102, 104 are positioned to permit the detector 106 to detect reflected light that is emitted from the light sources toward the skin and therefore the light sources and detector may be closely located on a miniature substrate within a housing, band or other protective elements of the monitoring device 100.

As seen in FIG. 2, the monitoring device 100 may further comprise a central processing unit (CPU) 110 coupled to a memory 112, display 114, bus 116, and one or more input/output (I/O) devices 120, and a wireless networking interface 124. Display 114 and/or I/O devices 120 may be omitted in certain embodiments. Display 114 may comprise a liquid crystal display, light-emitting diode display, touchscreen, or other electronic digital display device that a CPU can drive. Display 114 may be programmed or configured to display data, such as time, heart rate, and $SpO_2$ levels of a user. In an embodiment, the monitoring device 100 is a wristband and the display 114 is configured such that the display faces away from the outside of a user's wrist when the user wears the monitoring device. In other embodiments, the display 114 may be omitted and data detected by the monitoring device 100 may be transmitted using the wireless networking interface 124 via near-field communication (NFC), BLUETOOTH, WiFi, or other suitable wireless communication protocols to a host computer 900 for analysis, display and/or reporting.

I/O devices 120 may include, for example, motion sensors, vibration devices, lights, loudspeakers or sound devices, microphones, or other analog or digital input or output devices. Memory 112 may comprise RAM, ROM, FLASH memory or other digital data storage, and may include a control program 118 comprising sequences of instructions which when loaded from the memory and executed using the CPU 110 cause the CPU to perform the functions that are described herein. The light sources 102, 104 and detectors 106 may be coupled to bus 116 directly or indirectly using driver circuitry by which the CPU may drive the light sources and obtain signals from the detectors.

The host computer 900 may be coupled to the wireless networking interface 124 via one or more networks 128, which may include one or more local area networks, wide area networks, and/or internetworks using any of terrestrial or satellite links. In some embodiments, host computer 900 executes control programs and/or application programs that are configured to perform some of the functions described herein including but not limited to the processes described herein with respect to FIG. 6, FIG. 8.

Further, for purposes of illustrating a clear example, FIG. 1 depicts six pairs of light sources 102, two secondary light sources 104, and one detector 106, but in other embodiments the monitoring device 100 may contain any number of pairs of light sources 102, secondary light sources 104, and detectors 106.

In an embodiment, light sources 102, 104 and detectors 106 are configured to be aligned proximate to a user's skin when monitoring device 100 is worn. "Proximate" may mean any of slightly separated from, near, adjacent to, or in direct contact with, but direct contact is not required. For example, in FIG. 1, monitoring device 100 is worn on the wrist of a user such that light sources 102, 104 and detectors 106 are adjacent to the inner wrist of the user. The positioning of the monitoring device 100 as shown in FIG. 1 is provided merely as an example, and other embodiments may use alternative positioning. For example, the device may be positioned where light sources 102, 104 and detectors 106 are oriented on the outer wrist rather than the inner wrist. The monitoring device 100 may be formed with perimeter dimensions of different sizes that cause the light sources 102, 104 and detectors 106 to be in contact with the skin, or separated from the skin.

FIG. 5 illustrates a schematic perspective view of a monitoring device in one embodiment. In this embodiment, monitoring device 100 comprises a wrist band in which light sources 102, 104 and detectors 106 are mounted on or within an underside of monitoring device 100. Monitoring device 100 may include a fastening means to attach monitoring device to a portion of a user's body and the specific form of the fastening means is not critical. The fastening means may be a strap that is passed through a receiving portion of the strap and fastened with hook and/or loop fasteners. Other fastening means may include clips, latches, hook-and-loop fasteners such as VELCRO, clasps, ties, pegs, and/or adhesives. The fastening means may be located on any side of monitoring device 100 such that the fastening device does not interfere with movement or activity.

In an embodiment, the monitoring device 100 may comprise a processor, memory, user interface, wireless transceiver, one or more environmental sensors, and one or more biometric sensors other than the detectors 106. For example, embodiments may be implemented using a monitoring device of the type shown in U.S. Pat. No. 8,948,832 of Fitbit, Inc., San Francisco, Calif., the entire contents of which are hereby incorporated by reference for all purposes as if fully set forth herein. In other words, the monitoring device of the type shown in U.S. Pat. No. 8,948,832 could be modified based upon the additional disclosure herein to result in a working activity monitoring apparatus capable of performing the functions that are described herein. Therefore, the present disclosure presumes that the reader knows and understands U.S. Pat. No. 8,948,832, and this disclosure is directed to persons having a level of skill sufficient to modify or adapt the monitoring device of the type shown in U.S. Pat. No. 8,948,832 based upon the additional disclosure herein to result in a working activity monitoring apparatus capable of performing the functions that are described herein.

In an embodiment, the light sources 102 may comprise one or more pairs of electronic semiconductor light sources, such as light-emitting diodes (LEDs), which are laterally aligned on a substrate with detectors 106. For example, FIG. 1 and FIG. 5 depict three pairs of light sources 102 on either side of detectors 106. Light sources 102, 104 may be coupled to a power source or driver circuit.

In an embodiment, each pair of light sources 102 includes a red light source and an infrared light source. The light sources 102 may emit light with peak wavelengths typically in the range of 650 nm to 940 nm. For example, in various embodiments a particular red light source may emit light with a peak wavelength of 660 nm. The infrared light source may emit light with peak wavelengths in the range of 750 nm to 1700 nm. By way of example and not limitation, a particular infrared light source may emit light with a peak wavelength of 730 nm, 760 nm, 850 nm, 870 nm, or 940 nm. Commercial light sources such as LEDs tend to provide output at about 20 nm intervals with a center wavelength tolerance of +/−10 nm from the manufacturer's specified wavelength and thus one possible range of useful peak wavelengths for the light sources is 650 nm to 950 nm.

In an embodiment, the light sources 102 are mounted in positions that are spaced apart along the substrate. Pairs of light sources on one side of detectors 106 may be equally spaced from detectors 106 as corresponding pairs on an opposite side of detectors 106. Additionally and/or alternatively, pairs of light sources may be equally spaced from each other. For example, on one side of detectors 106, a first pair of light sources may be placed 1 mm from the detectors; a second pair of light sources may be placed 1 mm from the first light sources; and a third pair of light sources may be placed 1 mm from the second pair of light sources.

The spacing of the light sources may be measured from the side of the light source or the center of the light source. For example, the light sources may be configured such that the center of each light source of a first pair of light sources is 2 mm from the edge of detectors 106 and the center of each light source of a second pair of light sources is 2 mm from the center of a corresponding light source in the first pair of light sources. The particular magnitude of the spacing may depend on a number of factors and this disclosure does not limit the embodiments to any particular spacing. For example, spacing in a range of 1 mm (or less) to 10 mm would be workable in various embodiments.

The orientation of the light sources on either side of detectors 106 may be the same. For example, in the orientation depicted in FIG. 5, each pair of light sources may comprise a top light source comprising a red LED and a bottom light source comprising an infrared LED. In other embodiments, light sources on either side of detectors 106 may have opposite orientations. For example, FIG. 5 depicts light sources on one side of detectors 106 which comprise a top light source comprising a red LED while the light sources on the opposite side of detectors 106 comprise a top light source comprising an infrared LED.

Additionally and/or alternatively, light sources on one side of detectors 106 may have different orientations. For example, a first pair of light sources on one side of detectors 106 may comprise a top light source comprising a red LED and a second light source on the same side of detectors 106 may comprise a top light source comprising an infrared LED.

In an embodiment, light sources 104 may comprise one or more light sources that are longitudinally aligned on a fixed substrate with detectors 106. For example, FIG. 1 and FIG. 5 depict two light sources 104, one which is above the detectors 106 and one which is below the detectors 106. In an embodiment, light sources 104 may be green light sources, such as green LEDs. The green light sources may be configured to emit light with wavelengths in the range of 495 nm to 570 nm. For example, a particular green light source may emit light with a wavelength of 528 nm. The green light sources may be equally spaced from detectors 106 as the pairs of red and infrared light sources. For example, if the distance between detectors 106 and a center of a first red light source is 2 mm, the distance between detectors 106 and a green light source may also be 2 mm. Further, in some embodiments, one or more of the light sources 104 may comprise a single LED package that emits multiple wavelengths, such as green, red and infrared wavelengths, at the same location with respect to multiple detectors. Such LEDs may include multiple semiconductor elements co-located using a single die in a single packages, and therefore FIG. 1, FIG. 5 are not intended to imply that separate components in separate packages are required.

Detectors 106 are sensors adapted to detect wavelengths of light emitted from light sources 102, 104 and together with the light sources form sensors such as PPG sensors. A particular light source 102 combined with a particular detector 106 may comprise a sensor such as a PPG sensor. A first PPG sensor and a second PPG sensor can share components, such as the same light sources and/or detectors, or have different components and thus the term "PPG sensor" is used for simplicity of description although actual embodiments may use multiple components in implementing a PPG sensor. Detectors 106, in an embodiment, may comprise one or more detectors for detecting each different wavelength of light that is used by the light sources. For example, a first detector may be configured to detect light with a wavelength of 660 nm, a second detector may be configured to detect light with a wavelength of 940 nm, and a third detector may be configured to detect light with a wavelength of 528 nm. Examples include photodiodes fabricated from semiconductor materials and having optical filters that admit only light of a particular wavelength or range of wavelengths.

In other embodiments, detectors 106 comprise one or more detectors configured to detect multiple wavelengths of light. For example, a single detector may be configured to tune to different frequencies based on data received from an electrical digital microprocessor coupled to detectors 106. In another way, the single detector may include multiple active areas where each active area is sensitive to a given range of wavelengths. In an embodiment, a single detector is configured to detect light with wavelengths in the red and infrared frequencies and a second detector is configured to detect light with wavelengths in the green frequencies. Further, each of the light sources 102, 104 may use any of one or more different wavelengths of light as previously described.

In an embodiment, detectors 106 are mounted in a housing with one or more filters configured to filter out wavelengths of light other than wavelengths emitted by light sources 102, 104. For example, a first portion of the housing may be covered with a filter which removes ambient light other than light in wavelengths emitted by light sources 102 and a second portion of the housing may be covered with a filter which removes all ambient light other than light in wavelengths emitted by light sources 104. For example, signals from one or more PPG sensors may be received through an ambient light filter that filters out an ambient light source that generates an ambient light with a wavelength that is different from the wavelength that is detected by at least one of the sensors.

Figure 4:
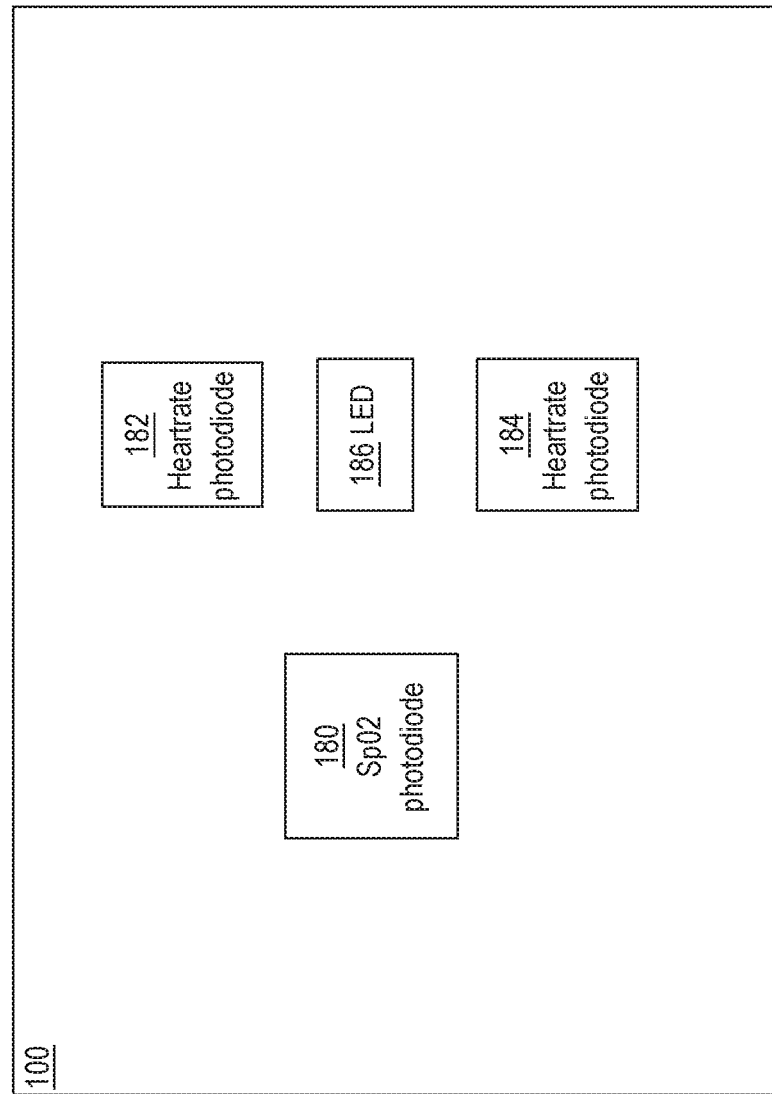
FIG. 4 illustrates an example topology of a light source and a plurality of detectors.

FIG. 4 illustrates an example topology of a light source and a plurality of detectors (e.g., photodiodes). FIG. 4 is shown in simplified, schematic format for purposes of illustrating a clear example. In an embodiment, a multi-color light-emitting diode (LED) 186 is affixed to a substrate within the monitoring device 100. A first photodiode 180 is located in a position on a first light path with respect to LED 186. Second and third photodiodes 182, 184 are located symmetrically opposite the LED and are aligned on light paths that are different from the first light path. In one embodiment, LED 186 is capable of emitting three (3) wavelengths of light in the red, infrared, and green portions of the spectrum, using multiple semiconductor devices within a single lens or package. The first photodiode 180 is configured to receive PPG signals based upon emission of red and infrared light and is used to produce a $SpO_2$ signal. The second and third photodiodes 182, 184 are configured to detect PPG signals based upon emission of green light and to generate a heart rate signal based on those PPG signals. The $SpO_2$ signal and heart rate signal may be processed in the manner that is described herein, for example, with respect to the flow diagrams and other functional descriptions.

3. Noise Reduction Through Other PPG Signals

A number of flow diagrams are presented herein to illustrate various methods that may be performed by example embodiments. The flow diagrams illustrate example algorithms that may be programmed, using any suitable programming environment or language, to create machine code capable of execution by a CPU or microcontroller of the monitoring device 100. In other words, the flow diagrams, together with the written description in this document, are disclosures of algorithms for aspects of the claimed subject matter, presented at the same level of detail that is normally used for communication of this subject matter among skilled persons in the art to which the disclosure pertains. Various embodiments may be coded using assembly, C, OBJECTIVE-C, C++, JAVA, or other human-readable languages and then compiled, assembled, or otherwise transformed into machine code that can be loaded into ROM, EPROM, or other recordable memory of the activity monitoring apparatus that is coupled to the CPU or microcontroller and then then executed by the CPU or microcontroller.

For purposes of illustrating a clear example, this disclosure may describe the methods with reference to the devices/components shown in other figures, such as FIGS. 1 and 2. However, other embodiments may be implemented using data from other sources and computers or apparatus other than those shown in the aforementioned figures.

Figure 3:
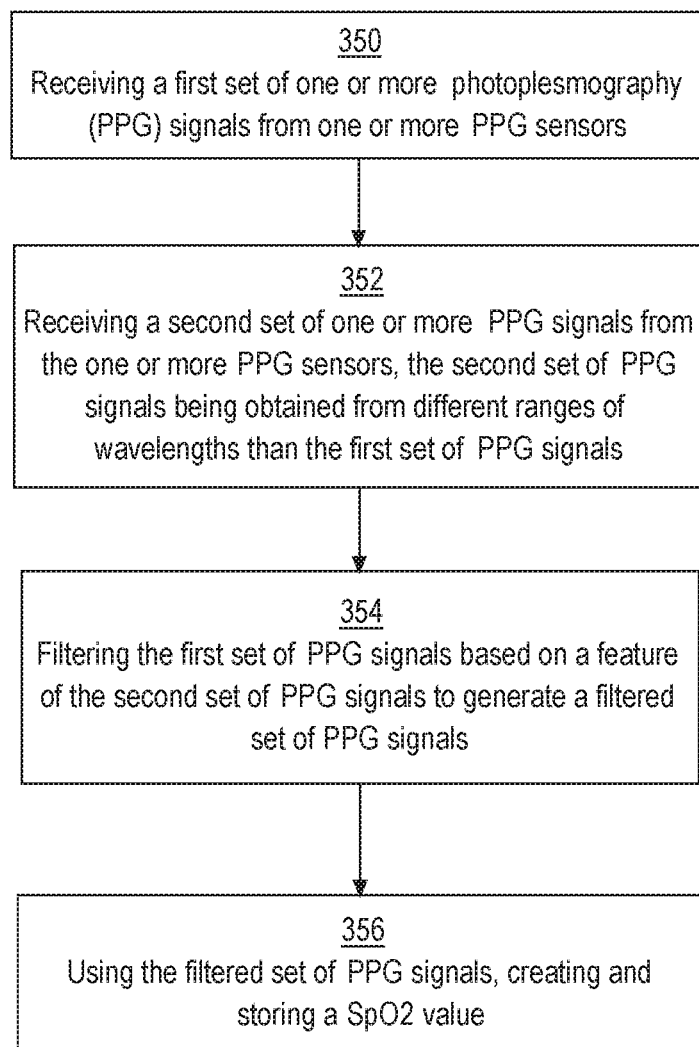
FIG. 3 illustrates an example method characterizing a heart rate using PPG signals for $SpO_2$ detection and PPG signals for heartrate.

To begin, FIG. 3 illustrates an example method for creating a $SpO_2$ value using a PPG signal as a reference signal to filter PPG signals used to determine the $SpO_2$ value.

The method shown in FIG. 3 may begin at block 350 when a monitoring device receives a first set of one or more PPG signals from one or more PPG sensors. The first set of PPG signals may be represented in any suitable form capable of being processed by a processor, such as the analog signals or digital data sampled from the analog components and stored in computer memory. In an example, the first set of PPG signals may correspond to red and/or infrared light previously emitted by a light source (or light sources) after the emitted light has interacted with a user's skin, when the monitoring device is worn. It is to be appreciated that the first set of PPG signals may include a noise component, as discussed above.

The method shown in FIG. 3 may continue at block 352 when the monitoring device receives a second set of one or more PPG signals from the one or more PPG sensors. Again, the second set of PPG signals may be represented in any suitable form capable of being processed by a processor, such as the analog signals or digital data sampled from the analog components and stored in computer memory. In an example, the second set of PPG signals is obtained from different ranges of wavelengths emitted from the light source than the first set of PPG signals. For example, the second set of PPG signals may be obtained from green light sources. In some cases, the second set of PPG signals is obtained from a system within the monitoring device used for tracking a user's heart rate. In other cases, the second set of PPG signals is received from a system separate from heart rate detection.

At block 354, the monitoring device filters the first set of PPG signals based on a feature of the second set of PPG signals to generate a filtered set of PPG signals. Various filtering techniques may be used, depending on embodiment, to remove noise or other features from the first set of PPG signals based on a feature of the second set of PPG signals. As one example, heart rate may be the feature of the second set of PPG signals. In the case of a heart rate, the monitoring device may create a filter based the detected frequency of the heart rate signal. Examples of filters include a low-pass filter, a high-pass filter, and a narrow band filter that excludes frequencies that are inconsistent with the frequency of the heart rate signal.

It is to be appreciated that, based on block 354, the monitoring device may use one range of wavelengths to better measure an underlying signal on which the wavelengths of the first set of PPG signals operates. Based on this underlying signal (or features derived therefrom), the monitoring device can improve the first set of PPG signals based on filtering noise from the first set of PPG signals.

Continuing with the method shown in FIG. 3, at block 356, the monitoring device may use the filtered set of PPG signals to create and store a $SpO_2$ value. As an example, the filtered set of PPG signals may have a reduced or eliminated noise component and therefore may serve as a more accurate basis for creating and storing the $SpO_2$ value.

Accordingly, the method shown in FIG. 3 illustrates a method for using a first set of PPG signals to detect an underlying signal to improve another set of PPG signals that may be used to determine a $SpO_2$ value. Alternative or specific embodiments are now discussed.

Figure 6:
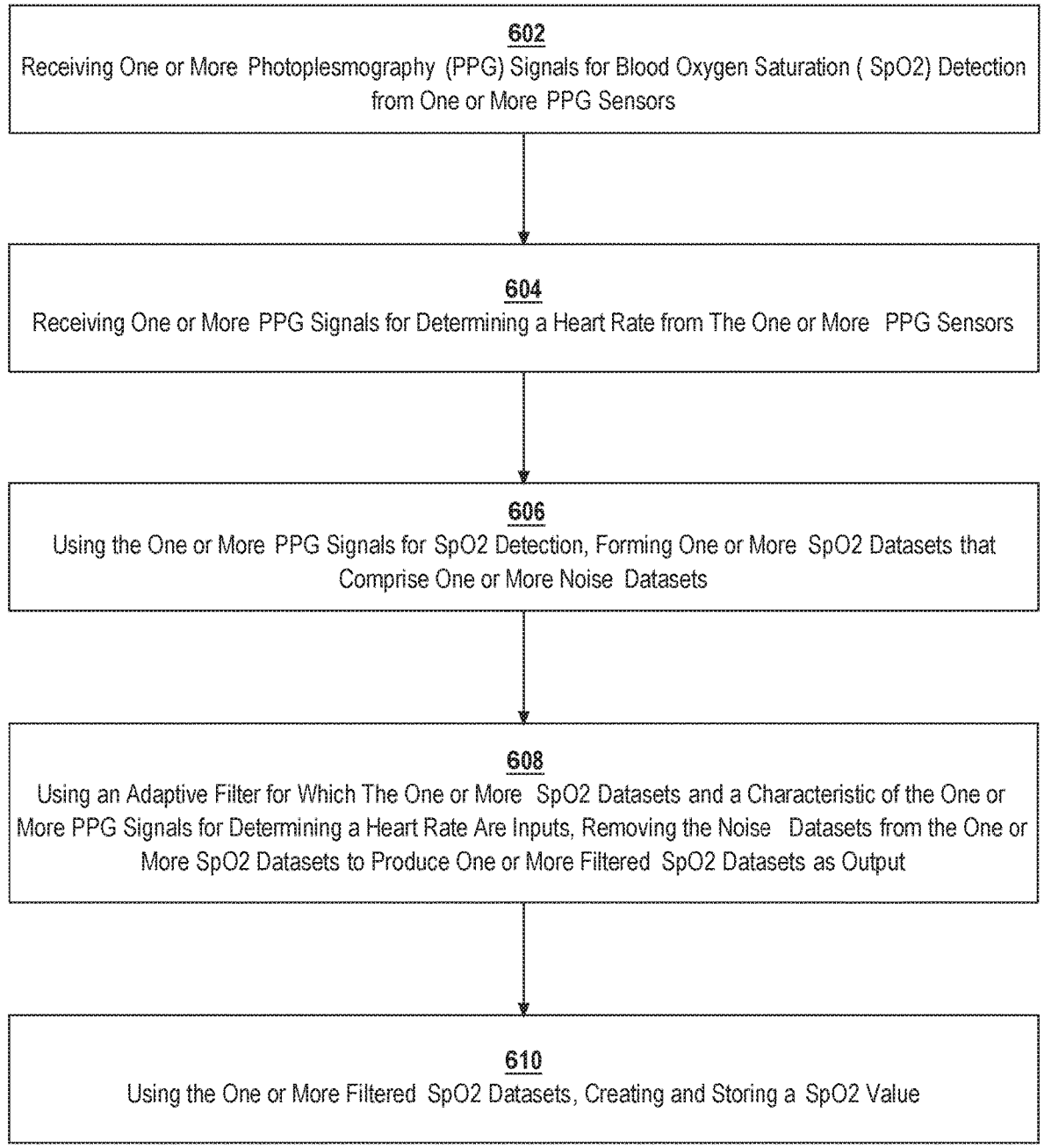
FIG. 6 illustrates a flow diagram of an example method for creating and storing a $SpO_2$ value using PPG signals for $SpO_2$ detection and PPG signals for characterizing a heart rate.

FIG. 6 illustrates a flow diagram of another method for creating and storing a $SpO_2$ value using PPG signals for $SpO_2$ and PPG signals for characterizing or determining a heart rate.

At step 602, one or more PPG signals for $SpO_2$ detection are received from one or more PPG sensors. For example, power from a power supply, such as a battery and power supply circuit, is coupled to red and infrared light sources 102, which are energized and, when the monitoring device is worn, produce light toward the skin that is proximate to blood vessels. Reflected light is detected using the detector 106 and PPG signals are formed using the detector 106 and gated or signaled for transient storage in memory within the monitoring device 100. Under program control, the CPU or microcontroller may load a set of PPG signals from the memory into registers or other data storage. The PPG signals may be obtained from the detectors based upon light sources operating at any of the frequencies that have been described above with respect to FIG. 1, FIG. 5.

At step 604, one or more PPG signals for characterizing a heart rate are received from the one or more PPG sensors. Step 604 may be implemented in the manner described above for step 602, except that, in some cases, the green light sources 104 are used and the PPG signals for characterizing a heart rate are formed based upon reflected green light that is detected using the detectors 106. The PPG signals for characterizing the heart rate may, in some cases, be suitable to represent an underlying signal from the PPG sensors. However, compared to the PPG signals for $SpO_2$ detection, the PPG signals for characterizing the heart rate may be obtained from a wavelength that better exhibits the underlying signal. In some cases, the PPG signals for characterizing a heart rate may be based upon detection of reflected green light from the green light sources. The PPG signals for characterizing the heart rate may characterize the heart rate in that one or more of the following features may be determinable: a fundamental frequency (e.g., of the green light), one or more different harmonic frequencies (e.g., of the green light), a template of the underlying signal (e.g., the green light), and the like.

As an alternative to using the green PPG signal from the monitoring device 100, a signal characteristic of a heart rate may be obtained from an entirely different apparatus, such as from an electrocardiogram (EKG) apparatus in real time, or from stored EKG data that is obtained from a server computer by direct retrieval from storage that is coupled to the server computer, or programmatically using an application program interface (API) call, or using any other suitable data retrieval operation. In other words, the heart rate signal that is used in adaptively filtering the red and infrared PPG signals need not come from the activity monitoring apparatus, and need not be received at the same time as the red and infrared signals; instead any other source of the heart rate signal may be used.

In some embodiments, the PPG signals for $SpO_2$ and heart rate may be correlated in time by interlacing or another form of multiplexing, and stored in that format. Thus various embodiments may store separate streams of PPG signal data for heart rate and $SpO_2$ or an integrated stream in which both kinds of data are interleaved or mixed. In some embodiments, the PPG signals that are used for determining characteristics of heart rate may be obtained from a system that measures a user's heart rate and is separate from the systems described herein. Such an embodiment may contribute PPG signals to the system disclosed herein, and those contributed signals then may be improved based upon the PPG signals for $SpO_2$ that are obtained using the system disclosed herein. For example, a medical-grade fingertip pulse oximetry device could be used to acquire PPG signals indicating pulse, and those signals may be received at a server computer that also obtains PPG signals for $SpO_2$ in the manner described herein. The server computer may be programmed to implement the noise removal and other signal improvement techniques described herein.

At step 606, one or more $SpO_2$ datasets are formed where the $SpO_2$ includes one or more noise components, using the one or more PPG signals for $SpO_2$ detection that have been obtained or received from detectors in any of the topologies for light sensors and detectors that are described herein. In an embodiment, under program control, the PPG signals that were received at step 602 are stored as $SpO_2$ datasets in digital memory. A "dataset," as used herein, may refer to a computer usable representation of data stored in computer memory. The dataset may be organized or otherwise structured to allow for a processor or program to access given elements of the datasets, such as an indexed (e.g., the Nth) sample of the PPG signal. In an example, the dataset may be stored in a buffer used for temporary processing or storing or in computer memory used for longer-term processing or storage.

In many cases, the PPG signals for $SpO_2$ and the corresponding $SpO_2$ datasets include a noise component. Noise may be introduced into a PPG signal, for example, from skin morphology of the wearer of the apparatus, the presence of hair, tattoos, fatty tissue, pathological conditions that result in weak blood circulation, movement of the device, or other conditions.

At step 608, the noise components are removed from the one or more $SpO_2$ datasets to produce one or more filtered $SpO_2$ datasets, which can be performed by using an adaptive filter for which the one or more $SpO_2$ datasets and a characteristic of the one or more PPG signals for characterizing a heart rate are inputs. For example, the $SpO_2$ datasets formed at step 606 may be filtered based upon the signals received at step 604 to remove all or part of noise components from the $SpO_2$ datasets to yield filtered $SpO_2$ datasets. In one embodiment, the PPG signals obtained using infrared and red light sources typically are weaker than signals based upon green light sources (e.g., see FIG. 7); however, a heart rate signal determined using the green light source may be used to improve the PPG signals with an adaptive filter that uses the heart rate information detected using the green light sources to remove noise that are inconsistent with the heart rate frequency. In an embodiment, the PPG signals for $SpO_2$ comprise primary inputs to an adaptive filter and the heart rate signal is the reference input.

With respect to the operation of removing the noise components, various embodiments may use least mean squares (LMS) filtering of the one or more $SpO_2$ datasets with the one or more PPG signals for heart rate, recursive least squares (RLS) filtering, and similar techniques, implemented in executable code in the monitoring device 100 or in host computer 900 that is processing data received from the monitoring device. Other example techniques include creating a template from a high-quality PPG signal to use as filter coefficients for a matched filter to maximize signal to noise in the presence of additive, stochastic noise. Yet another technique is using an adaptive filter that tunes a band-pass in real-time based upon heartbeat data derived from the PPG datasets, usually based upon green light sources. Correlation computations may be computed between $SpO_2$ datasets obtained from red or infrared light sources and PPG signals obtained from green light sources, to identify motion artifacts. Thus one embodiment may comprise using the adaptive filter with one or more $SpO_2$ datasets and a feature of the one or more PPG signals for characterizing a heart rate as inputs, and removing the noise components from the one or more $SpO_2$ datasets, that are inconsistent with a characteristic of the heart rate frequency PPG signal, to produce one or more filtered $SpO_2$ datasets as output, using a least mean squares fitting or recursive least squares fitting of the one or more $SpO_2$ datasets to the heart rate frequency PPG signal.

The utility of step 608 may be further understood with reference to FIG. 7. FIG. 7 is a two-part graph that illustrates example PPG signals before and after removal of noise based upon a heart rate information. A first graph at the top of FIG. 7 depicts lines representing green, red, and infrared PPG signals obtained from detection of reflected light from green, red, and infrared light sources respectively, illustrated as amplitude versus time. It will be seen that the red and infrared signals include significant noise components expressed as repeated short changes in amplitude over a given time span. The green signal exhibits a sharp upward peak, and the peak-to-peak distance may be used to determine a likely true heart rate frequency of the subject. An adaptive filter, tuned to the heart rate frequency, may be used to smooth or remove noise that is located around the peak points of the green signal when superimposed on the red and infrared signals. As seen in the second graph at the top of FIG. 7, this form of filtering results in outputting a filtered red PPG signal and a filtered infrared PPG signal that are smoother and therefore more accurate in indicating $SpO_2$ data.

With reference back to FIG. 6, at step 610, an $SpO_2$ value is created and stored using the one or more filtered $SpO_2$ datasets; the resulting value may be stored in memory of the monitoring device 100 or the host computer 900. An "$SpO_2$ value," as used herein, may refer to a metric that estimates a user's $SpO_2$ level or changes in the user's $SpO_2$ level. Thus some embodiments may generate metrics representing absolute $SpO_2$ values or relative changes in $SpO_2$.

The result of the method 600 can be a more accurate $SpO_2$ value. Further, the infrared and red light PPG signals may be processed with more robustness to noise, and therefore the monitoring device 100 may be designed or engineered to accommodate less strict noise floor requirements. For example, the monitoring device may be, in some cases, capable of accommodating a less snug attachment to the body, and/or the monitoring device may, in some cases, be capable of accommodating hair and skin conditions, or other noise sources that can interfere with the monitoring device when mounted on the body.

It is to be appreciated that the method 600 may be performed by one or more of: firmware operating on the monitoring device or a secondary device (e.g., a mobile device paired to the monitoring device, a server, or the like). For example, the monitoring device may execute operations relating to generating the PPG signals (for $SpO_2$ detection and for characterizing a heart rate), which, in turn, are uploaded or otherwise communicated to a server that performs operations for removing the noise data sets and creating the $SpO_2$ value. Alternatively, the monitoring device may execute operations relating to generating the PPG signals (for $SpO_2$ detection and for characterizing a heart rate) and removing the noise data sets to produce the filtered $SpO_2$ datasets. In this case, the filtered $SpO_2$ datasets are uploaded or otherwise communicated to a server that performs operations for creating the $SpO_2$ value. As another alternative, the monitoring device may execute each operation described with reference to the method 600 shown in FIG. 6.

4. Multiple Emitters with Spacing

In an embodiment, the use of multiple light sources or other emitters in configurations that are spaced differently with respect to the detector permits the monitoring device 100 to control the effective detector-emitter spacing to optimize for signal strength under various user skin conditions, by activating different pairs of red and infrared emitters. As the detector-emitter spacing increases, for example, a light path between the emitter and detector samples tissue content over a longer and deeper path, thereby improving signal strength. For example, users who exhibit periods of time of low perfusion, due to conditions such as cooling of the skin, may benefit from increasing the emitter-detector spacing automatically under program control, by activating the red light sources and infrared light sources that are farther away from the detector. The same effect can be obtained using a single emitter and a plurality of detectors.

Figure 8:
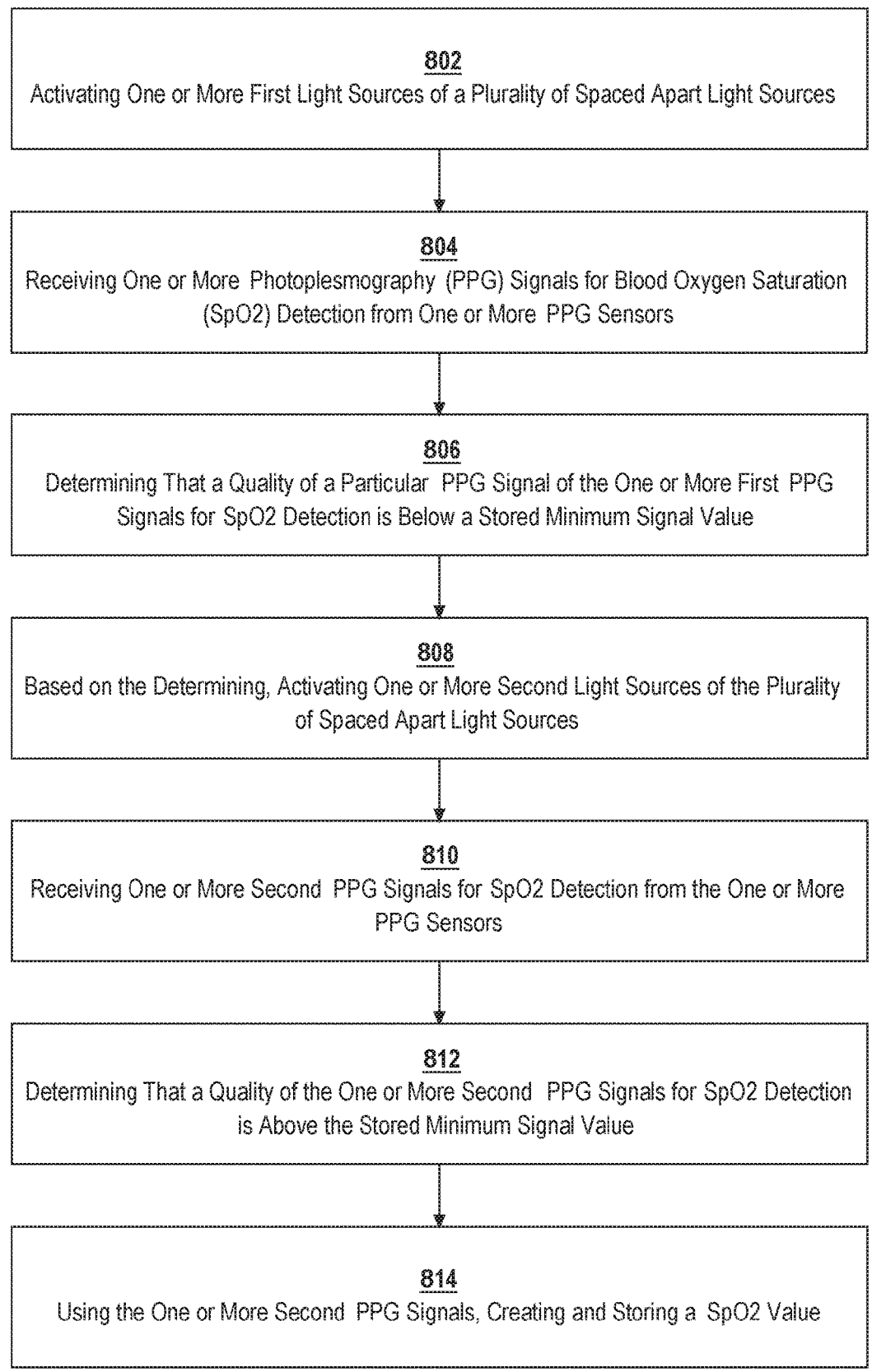
FIG. 8 illustrates a flow diagram of a method for creating and storing a $SpO_2$ value using a plurality of spaced apart light sources, in accordance with an example.

FIG. 8 illustrates a flow diagram of a method for creating and storing a SpO$_2$ value using a plurality of spaced apart light sources.

At step 802, one or more first light sources of a plurality of spaced apart light sources are activated. For example, step 802 may comprise using the CPU to signal a display driver circuit to energize a first pair of red and infrared light sources in the monitoring device 100.

At step 804, one or more first PPG signals for SpO$_2$ detection are received from one or more PPG sensors. Step 804 may comprise operations similar to those described above for step 602 (FIG. 6).

At step 806, a quality of a particular PPG signal of the one or more first PPG signals for SpO$_2$ detection is determined to be below a stored minimum signal value. Step 806 may comprise the CPU 110 (FIG. 2) comparing a stored threshold value, which represents a minimum acceptable signal value, to the amplitude of the PPG signals received at step 804.

At step 808, based on determining that the quality of the particular PPG signal is below the stored minimum signal value, one or more second light sources of the plurality of spaced apart light sources are activated. For example, step 808 may comprise the CPU signaling the display driver circuit to energize a second pair of red and infrared light sources at a different second position from the first pair.

Further, using these techniques, an embodiment of FIG. 8 may comprise: activating only a first pair of two or more pairs of light sources, and deactivating one or more other pairs; receiving, from one or more detectors, a first red PPG signal and a first infrared PPG signal from only the first pair of two or more pairs of red light sources and infrared light sources; determining that a first red PPG signal quality is below a stored minimum red PPG signal value or that a first infrared PPG signal quality is below a stored minimum infrared PPG signal value; and based on the determining, activating a second pair of the two or more pairs of red light sources and infrared light sources, receiving from the one or more detectors a second red PPG signal and a second infrared PPG signal associated with the second pair; determining that a second red PPG signal quality is above the stored minimum red PPG signal value and that the second infrared PPG signal quality is above the stored minimum infrared PPG signal quality value; using the second red PPG signal and the second infrared PPG signal as the one or more PPG signals for SpO$_2$ detection, determining one or more SpO$_2$ datasets. In some embodiments, the first signals that were used for quality determination are discarded or deleted from memory in favor of using the second signals, but this step is not required in all embodiments.

At step 810, one or more second PPG signals for SpO$_2$ detection are received from the one or more PPG sensors. Step 810 may comprise obtaining signals from the second pair of light sources as well as the first pair of light sources. At step 812, a quality of the one or more second PPG signals for SpO$_2$ is determined to be above the stored minimum signal value. At step 814, a SpO$_2$ value is created and stored using the one or more second PPG signals.

Additionally or alternatively, the process of FIG. 8 may receive input from biometric sensors or environmental sensors indicating an ambient temperature or a skin temperature of the wearer of the activity monitoring apparatus. Based on changes in temperature values received from these sensors, the process may energize or de-energize different pairs of light sources. In this embodiment, the process of FIG. 8 may include: activating only a first pair of two or more pairs of red light sources and infrared light sources, and deactivating all other pairs; receiving, from the one or more detectors, a first red PPG signal and a first infrared PPG signal from only the first pair of the two or more pairs of red light sources and infrared light sources; receiving an ambient temperature signal from an ambient temperature sensor that is located proximate to the two or more first pairs; determining that the ambient temperature signal is less than a stored minimum temperature signal; based on the determining, activating a second pair of the two or more pairs of red light sources and infrared light sources, receiving from the one or more detectors a second red PPG signal and a second infrared PPG signal associated with the second pair, forming a combined red PPG signal using the first red PPG signal and the second red PPG signal, and forming a combined infrared PPG signal using the first infrared PPG signal and the second infrared PPG signal.

The process of FIG. 8 may include a feedback loop and other test operations that result in selectively energizing or de-energizing different pairs of red and infrared light sources of the monitoring device 100 as ambient conditions change. For example, the process of FIG. 8 may be implemented as part of a continuous loop that is active whenever the monitoring device 100 is powered on, and may include operations to de-energize the second pair of light sources when signals received from the first pair of light sources are determined to be greater than the stored minimum signal value. Further, the process as a whole may be repeated for any one or more pairs of the light sources, so that the process results in energizing three or more pairs of light sources at any one time. In this manner, over time, different combinations of pairs may be energized or de-energized dynamically in response to changing ambient conditions, changing skin temperature, movement of the monitoring device 100 on the body of the user, or other conditions that result in changes in the strength of signals from the light sources.

5. Other Arrangements of Light Sources and/or Detectors

In an embodiment, light sources 102 are positioned on a rotatable substrate proximate to detectors 106. The rotatable substrate may be communicatively coupled to an electrical digital microprocessor and configured to alter a position of one or more pairs of light sources 102. The rotatable substrate may move pairs of light sources 102 laterally or may rotate pairs of light sources 102 around an axis. For example, FIG. 5 depicts three pairs of light sources 102 on either side of detectors 106. The rotatable substrate may be configured to shift a single pair of light sources 102 to the different positions depicted in FIG. 5. As another example, the rotatable substrate may be configured to flip the positions of each light source of a pair of light sources, such that a red light sources switches positions with an infrared light source.

The rotatable substrate may comprise a flat disk formed of metal or plastic that is affixed to a driving mechanism that is operable under control of the processor using a geared mechanism, or using electromagnetic means. For example, two or more points spaced apart around the circumference or perimeter of the substrate may comprise fixed rare earth magnets and the processor may be coupled to a single electromagnetic coil that may be energized at a first polarity or second polarity, which induces within the coil a magnetic field of a first polar orientation or a second polar orientation; using this means one of the magnets on the rotatable substrate will be alternatively attracted to or repelled from the coil, resulting in rotated or lateral motion of the substrate to an opposite circumferential position.

In an embodiment, a plurality of the light sources 102 may be positioned around one or more detectors, on a planar substrate that is circular or having other geometry, at different fixed angles with respect to one or more detectors at a center of the substrate or arranged at different angles around the substrate near the light sources. The light sources may be single-color, arranged in pairs such as red-infrared, red-green, or infrared-green. In this arrangement, the control program 118 may be programmed to selectively drive different light sources at different angular positions with respect to the detectors, and to test the quality of data resulting from driving those light sources. For example, the control program 118 may be configured to iterate through a plurality of different combinations of angular positions of light sources, while testing the amplitude of signals obtained via each combination, and to select a particular combination of light sources that is providing the signals of greatest amplitude. In this manner, over time, different combinations of light sources or pairs may be energized or de-energized dynamically in response to changing ambient conditions, changing skin temperature, movement of the monitoring device 100 on the body of the user, or other conditions that result in changes in the strength of signals from the light sources.

In these embodiments, the processes of FIG. 6, FIG. 8 may be implemented with additional operations that drive repositioning the rotatable substrate. For example, referring to FIG. 8, step 808 may comprise using the processor to energize the coil using a first particular polarity, thereby causing the rotatable substrate to rotate other light sources into position.

6. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 9:
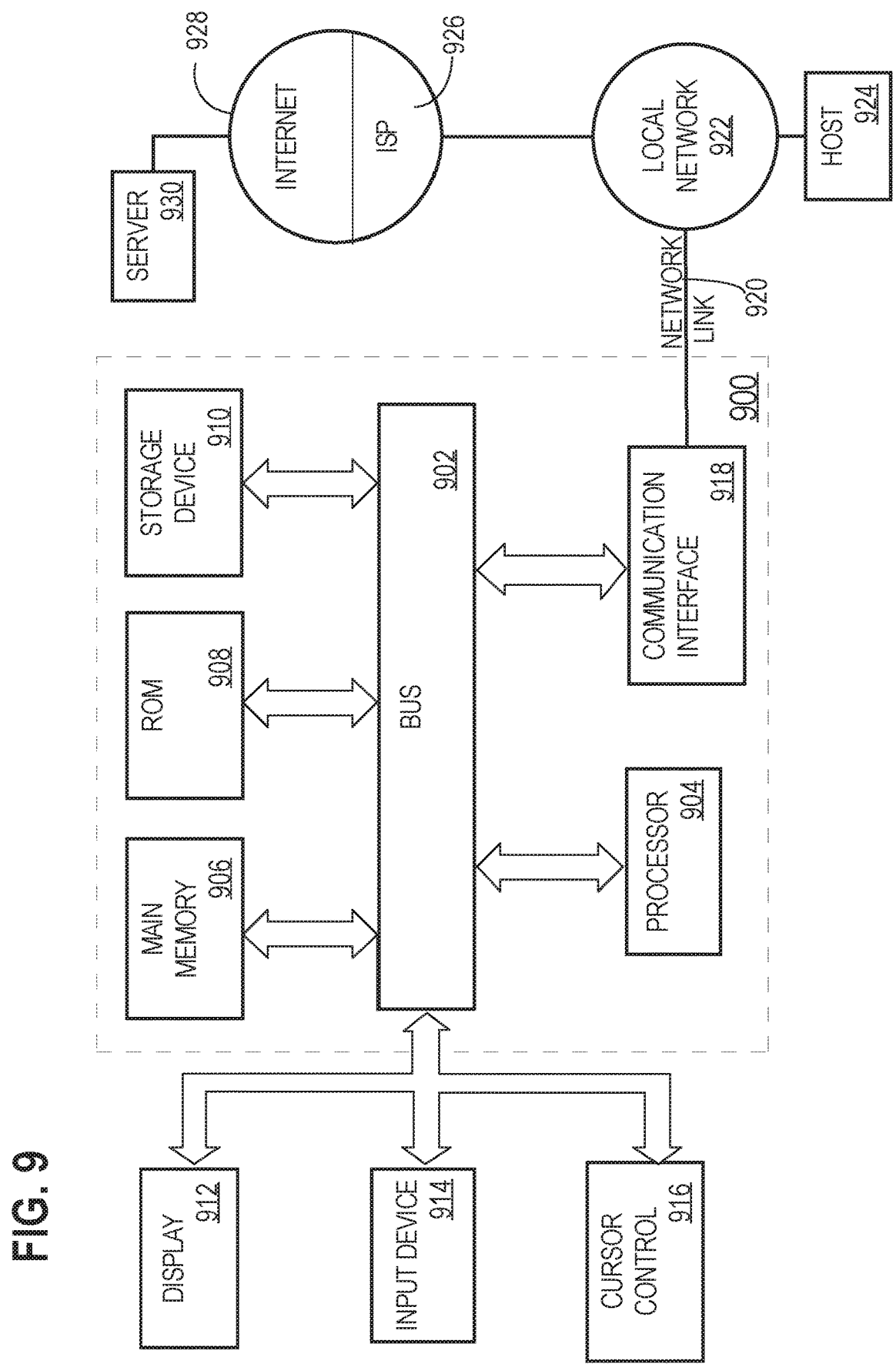
FIG. 9 illustrates an example computer system that may be specially configured to perform various techniques described herein.

For example, FIG. 9 is a block diagram that illustrates a computer system 900 upon which an embodiment may be implemented. Computer system 900 includes a bus 902 or other communication mechanism for communicating information, and a hardware processor 904 coupled with bus 902 for processing information. Hardware processor 904 may be, for example, a general purpose microprocessor.

Computer system 900 also includes a main memory 906, such as a random access memory (RAM) or other dynamic storage device, coupled to bus 902 for storing information and instructions to be executed by processor 904. Main memory 906 also may be used for storing temporary variables or other intermediate information during execution of instructions to be executed by processor 904. Such instructions, when stored in non-transitory storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk, optical disk, or solid-state drive is provided and coupled to bus 902 for storing information and instructions.

Computer system 900 may be coupled via bus 902 to a display 912, such as a cathode ray tube (CRT), for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

Computer system 900 may implement the techniques described herein using customized hard-wired logic, one or more ASICs or FPGAs, firmware and/or program logic which in combination with the computer system causes or programs computer system 900 to be a special-purpose machine. According to one embodiment, the techniques herein are performed by computer system 900 in response to processor 904 executing one or more sequences of one or more instructions contained in main memory 906. Such instructions may be read into main memory 906 from another storage medium, such as storage device 910. Execution of the sequences of instructions contained in main memory 906 causes processor 904 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 910. Volatile media includes dynamic memory, such as main memory 906. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 902. Transmission media can also take the form of acoustic or light waves, such as those generated during radio-wave and infra-red data communications.

Various forms of media may be involved in carrying one or more sequences of one or more instructions to processor 904 for execution. For example, the instructions may initially be carried on a magnetic disk or solid-state drive of a remote computer. The remote computer can load the instructions into its dynamic memory and send the instructions over a telephone line using a modem. A modem local to computer system 900 can receive the data on the telephone line and use an infra-red transmitter to convert the data to an infra-red signal. An infra-red detector can receive the data carried in the infra-red signal and appropriate circuitry can place the data on bus 902. Bus 902 carries the data to main memory 906, from which processor 904 retrieves and executes the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. As another example, communication interface 918 may be a local area network (LAN) card to provide a data communication connection to a compatible LAN. Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to another host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918.

The received code may be executed by processor 904 as it is received, and/or stored in storage device 910, or other non-volatile storage for later execution.

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. An apparatus comprising:
a housing;
a plurality of biometric sensors located in the housing, the plurality of biometric sensors including at least a first biometric sensor configured to provide first biometric data and a second biometric sensor configured to produce second biometric data, wherein:
the first biometric data is different from the second biometric data,
the second biometric sensor includes three or more devices,
each device is selected from the group consisting of a light detector and a light emitter, the three or more devices include at least one light detector and at least one light emitter,
the three or more devices are arranged to provide at least two different detector-emitter spacings,
each detector-emitter spacing is associated with a device pair,
each device pair includes one of the three or more devices that is a light detector and one of the three or more devices that is a light emitter, and
the detector-emitter spacing for each device pair represents a distance between the light detector and the light emitter for that device pair; and
one or more processors communicatively coupled with a memory, wherein the memory stores computer-executable instructions which, when executed by the one or more processors, cause the one or more processors to:
obtain the first biometric data from the first biometric sensor, and
select, based on the first biometric data, a first set of one or more of the device pairs having a first detector-emitter spacing,
cause each light emitter in the first set of one or more of the device pairs to emit light,
obtain one or more first signals from the light detector or light detectors of the first set of one or more of the device pairs while each light emitter of the first set of the one or more of the device pairs emits light, and
generate the second biometric data based, at least in part, on the one or more first signals.

2. The apparatus of claim 1, wherein the first detector-emitter spacing is greater than at least one other detector-emitter spacing associated with the device pairs of the second biometric sensor.

3. The apparatus of claim 1, wherein the memory stores further computer-executable instructions which, when executed by the one or more processors, further cause the one or more processors to:
select a second set of one or more of the device pairs having a second detector-emitter spacing,
cause each light emitter in the second set of one or more of the device pairs to emit light,
obtain one or more second signals from the light detector or light detectors of the second set of one or more of the device pairs while each light emitter of the second set of one or more of the device pairs emits light, and
generate the second biometric data based, at least in further part, on the one or more second signals, wherein the first detector-emitter spacing is different from the second detector-emitter spacing.

4. The apparatus of claim 3, wherein the first detector-emitter spacing is greater than the second detector-emitter spacing.

5. The apparatus of claim 4, wherein the first detector-emitter spacing is at least twice as large as the second detector-emitter spacing.

6. The apparatus of claim 5, wherein the second detector-emitter spacing is approximately 2 mm and the first detector-emitter spacing is approximately 4 mm.

7. The apparatus of claim 5, wherein the second detector-emitter spacing is approximately 1 mm and the first detector-emitter spacing is approximately 2 mm.

8. The apparatus of claim 3, wherein:
the first set of one or more of the device pairs includes a first device pair and a second device pair,
the second set of one or more of the device pairs includes a third device pair and a fourth device pair,
the light emitters of the first device pair and the third device pair are both configured to primarily emit red light,
the light emitters of the second device pair and the fourth device pair are both configured to primarily emit infra-red light, and
the memory stores further computer-executable instructions which, when executed by the one or more processors, further cause the one or more processors to:
combine the first signal that is obtained while the light emitter of the first device pair is emitting light with the second signal that is obtained while the light emitter of the third device pair is emitting light to form a first combined signal, and
combine the first signal that is obtained while the light emitter of the second device pair is emitting light with the second signal that is obtained while the light emitter of the fourth device pair is emitting light to form a second combined signal.

9. The apparatus of claim 8, wherein the memory stores further computer-executable instructions which, when executed by the one or more processors, further cause the one or more processors to:
cause each light emitter in the first set of one or more of the device pairs to emit the light in the absence of light emission from light emitters not in the first set of one or more of the device pairs, and
cause each light emitter in the second set of one or more of the device pairs to emit the light in the absence of light emission from light emitters not in the second set of one or more of the device pairs.

10. The apparatus of claim 8, wherein the memory stores further computer-executable instructions which, when executed by the one or more processors, further cause the one or more processors to:
cause the light emitters of the first device pair and the third device pair that are configured to primarily emit red light to emit light at least partially concurrently, and
cause the light emitters of the second device pair and the fourth device pair that are configured to primarily emit infrared light to emit light at least partially concurrently.

11. The apparatus of claim 8, wherein:
the second biometric data is an $SpO_2$ measurement, and
the memory stores further computer-executable instructions which, when executed by the one or more processors, further cause the one or more processors to determine the $SpO_2$ measurement using the first combined signal and the second combined signal.

12. The apparatus of claim 1, wherein:
the second biometric sensor includes at least a light detector, a first light emitter, and a second light emitter, and
the light detector and the first light emitter form a first device pair having a first detector-emitter spacing, and
the light detector and the second light emitter form a second device pair having a second detector-emitter spacing different from the first detector-emitter spacing.

13. The apparatus of claim 1, wherein:
the second biometric sensor includes at least a light emitter, a first light detector, and a second light detector, and
the light emitter and the first light detector form a first device pair having a first detector-emitter spacing, and
the light emitter and the second light detector form a second device pair having a second detector-emitter spacing different from the first detector-emitter spacing.

14. The apparatus of claim 1, wherein:
there are at least two device pairs that have the same detector-emitter spacing, and
the at least two device pairs that have the same detector-emitter spacing include one device pair that includes a light emitter that is configured to primarily emit red light and another device pair that includes a light emitter that is configured to primarily emit infrared light.

15. The apparatus of claim 14, wherein:
there are multiple sets of two device pairs where the two device pairs in each set have the same detector-emitter spacing and the detector-emitter spacings for each set of two device pairs is different from the detector-emitter spacing of the other sets, and
the at least two device pairs that have the same detector-emitter spacing include one device pair that includes a light emitter that is configured to primarily emit red light and another device pair that includes a light emitter that is configured to primarily emit infrared light.

16. The apparatus of claim 1, wherein the first biometric sensor is a temperature sensor and the first biometric data is temperature data.

17. The apparatus of claim 1, wherein the first biometric sensor is a sensor configured to detect relative movement between the apparatus and a body of a user and the first biometric data is indicative of movement between the apparatus and the body of the user.

* * * * *